US009260393B2

(12) United States Patent
Becker et al.

(10) Patent No.: US 9,260,393 B2
(45) Date of Patent: Feb. 16, 2016

(54) SOLID STATE FORMS OF N-((S)-2,3-DIHYDROXY-PROPYL)-3-(2-FLUORO-4-IODO-PHENYLAMINO)-ISONICOTINAMIDE

(71) Applicant: Merck Patent GmbH, Darmstadt (DE)

(72) Inventors: Axel Becker, Darmstadt (DE); Christoph Saal, Otzberg (DE); Clemens Kuehn, Darmstadt (DE); Donald Bankston, Dracut, MA (US); Marco Poma, Rome (IT)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/404,060

(22) PCT Filed: May 7, 2013

(86) PCT No.: PCT/EP2013/001352
§ 371 (c)(1),
(2) Date: Nov. 26, 2014

(87) PCT Pub. No.: WO2013/178320
PCT Pub. Date: Dec. 5, 2013

(65) Prior Publication Data
US 2015/0152059 A1    Jun. 4, 2015

Related U.S. Application Data

(60) Provisional application No. 61/653,037, filed on May 30, 2012.

(51) Int. Cl.
*C07D 213/81* (2006.01)
*A61K 31/44* (2006.01)

(52) U.S. Cl.
CPC .................................. *C07D 213/81* (2013.01)

(58) Field of Classification Search
None
See application file for complete search history.

(56) References Cited

U.S. PATENT DOCUMENTS

| 7,956,191 | B2 | 6/2011 | Abel et al. |
| 8,198,457 | B2 | 6/2012 | Abel et al. |
| 8,524,911 | B2 | 9/2013 | Abel et al. |
| 8,841,459 | B2 | 9/2014 | Abel et al. |
| 2009/0093462 | A1 | 4/2009 | Abel et al. |
| 2011/0224192 | A1 | 9/2011 | Abel et al. |
| 2012/0295889 | A1 | 11/2012 | Abel et al. |
| 2014/0051686 | A1 | 2/2014 | Abel et al. |

FOREIGN PATENT DOCUMENTS

WO    2006045514 A1    5/2006

OTHER PUBLICATIONS

Morissette et al, Advanced Drug Delivery Reviews, 56 (2004), pp. 275-300.*
International Search Report from PCT Application No. PCT/EP2013/001352 dated Aug. 29, 2013.
Kihyun Kim et al. "Blockade of the MEK/ERK signalling cascade by AS703026, a novel selective MEK1/2 inhibitor, induces pleiotropic anti-myeloma activity in vitro and in vivo" British Journal of Haematology, [2010], vol. 149, pp. 537-549.

* cited by examiner

*Primary Examiner* — Zinna Northington Davis
(74) *Attorney, Agent, or Firm* — Millen, White, Zelano and Branigan, P.C.

(57) ABSTRACT

The invention relates to solid state forms of N—((S)-2,3-Dihydroxy-propyl)-3-(2-fluoro-4-iodo-phenylamino)-isonicotinamide, processes for their preparation, and medical uses thereof.

16 Claims, 21 Drawing Sheets

Powder X-ray diffractogram of Form A1

(Cu-K$\alpha_1$ radiation, $\lambda$ = 1.5406 Å, Stoe StadiP 611 KL diffractometer)

Single crystal structure of Form A1 viewed along a-axis (XCalibur diffractometer from Oxford Diffraction equiped with graphite monochromator and CCD Detector using Mo K$_\alpha$ radiation at 301 K)

FTIR spectrum of Form A1

FT Raman spectrum of Form A1

DSC scan of Form A1

TGA scan of Form A1

Water Vapour Sorption Isotherm (25 °C) of Form A1

Powder X-ray diffractogram of Form A2
(Cu-K$\alpha_1$ radiation, $\lambda$ = 1.5406 Å, Stoe StadiP 611 KL diffractometer)

Crystal structure of Form A2 (calculated from Powder data) viewed along c-axis

FTIR spectrum of Form A2

FT Raman spectrum of Form A2

DSC scan of Form A2

TGA scan of Form A2

Water Vapour Sorption Isotherm (25 °C) of Form A2

Powder X-ray diffractogram of Form A-NF3

Powder X-ray diffractogram of Form A-NF6

Powder X-ray diffractogram of Form A-NF9

Powder X-ray diffractogram of Form A-NF10

Powder X-ray diffractogram of Form A-NF11

Powder X-ray diffractogram of Form B1

(Cu-Kα₁ radiation, λ = 1.5406 Å, Stoe StadiP 611 KL diffractometer)

Crystal structure of Form B1 (calculated from Powder data) viewed along c-axis

FTIR spectrum of Form B1

FT Raman spectrum of Form B1

DSC scan of Form B1

TGA scan of Form B1

Water Vapour Sorption Isotherm (25 °C) of Form B1

Powder X-ray diffractogram of Form B2

(Cu-K$\alpha_1$ radiation, $\lambda$ = 1.5406 Å, Stoe StadiP 611 KL diffractometer)

Crystal structure of Form B2 (calculated from Powder data) viewed along a-axis

FTIR spectrum of Form B2

FT Raman spectrum of Form B2

DSC scan of Form B2 (Type 1)

TGA scan of Form B2 (Type 1)

DSC scan of Form B2 (Type 2)

TGA scan of Form B2 (Type 2)

Water Vapour Sorption Isotherm (25 °C) of Form B2

Powder X-ray diffractogram of Form B-S1

Powder X-ray diffractogram of Form B-S2

SOLID STATE FORMS OF N-((S)-2,3-DIHYDROXY-PROPYL)-3-(2-FLUORO-4-IODO-PHENYLAMINO)-ISONICOTINAMIDE

CONTINUING DATA

This application is a 371 of PCT/EP2013/001352 filed May 7, 2013 which claims benefit of 61/653,037 filed May 30, 2012.

FIELD OF THE INVENTION

The invention relates to solid state forms of N—((S)-2,3-Dihydroxy-propyl)-3-(2-fluoro-4-iodo-phenylamino)-isonicotinamide, processes for their preparation, and medical uses thereof.

SUMMARY OF THE RELATED ART

N—((S)-2,3-Dihydroxy-propyl)-3-(2-fluoro-4-iodo-phenylamino)-isonicotinamide, for ease of reference hereinafter referred to as Compound C, its use as a kinase inhibitor to treat cancer, and its manufacture is disclosed in WO 2006/045514, page 76, Example 115. However, no solid state form of Compound C is disclosed in WO 2006/045514, or has been otherwise publicly disclosed to the best of applicants' knowledge, until the present date. Without a solid state form, however, it is not possible to provide a pharmaceutical active ingredient in a tablet, which is the dosage form of choice in terms of manufacturing, packaging, stability and patient compliance.

Therefore, in order to advance the development of Compound C as a drug substance, there is a high need to provide at least one solid state form of this compound.

DESCRIPTION OF THE INVENTION

Surprisingly, the inventors of the present patent application for the first time succeeded to provide a number of solid state forms of C that are not only crystalline but also stable, i.e. do not convert to other forms under the conditions of tablet manufacturing and storage.

In one specific aspect the invention relates to crystalline forms A1 and A2 of the mono hydrochloride of C. In another specific aspect the invention relates to crystalline forms B1 and B2 of the free base of C.

The crystalline forms are characterized, e.g., by x-ray powder diffractometry, single crystal diffractometry, FT IR spectroscopy, FT Raman spectroscopy, differential scanning calorimetry (DSC) and thermogravimetric analysis (TGA) as hereinafter shown in the experimental section.

All forms are characterized by high crystallinity, absence of hygroscopicity and high thermal stability. Moreover, forms A1 and A2 show a higher solubility and faster dissolution kinetics as compared to forms B1 and B2.

Furthermore, the present invention relates to pharmaceutical compositions comprising a solid state form of the present invention, together with at least one pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as pharmaceutical active ingredients.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, including non-small cell lung cancer, colon, colorectal, epidermoid, squamous cell, bladder, gastric, pancreatic, breast, head & neck, renal, kidney, liver, ovarian, prostate, uterine, oesophageal, testicular, gynecological, including endometrial, thyroid cancer, melanoma, including NRAS or BRAF mutated melanoma, as well as hematologic malignancies such as acute myelogenous leukemia, multiple myeloma, chronic myelogneous leukemia, myeloid cell leukemia, Kaposi's sarcoma, or any other type of solid or liquid tumors. Preferably, the cancer to be treated is chosen from colon, lung, breast and hematological tumor types.

Therefore, the present invention relates also to the use of the herein disclosed solid state forms of Compound C for the treatment of the above mentioned diseases.

The anti-cancer treatment defined above may be applied as a monotherapy or may involve, in addition to the herein disclosed solid state forms of Compound C, conventional surgery or radiotherapy or medicinal therapy. Such medicinal therapy, e.g. a chemotherapy or a targeted therapy, may include one or more, but preferably one, of the following anti-tumor agents:

Alkylating Agents
Such as altretamine, bendamustine, busulfan, carmustine, chlorambucil, chlormethine, cyclophosphamide, dacarbazine, ifosfamide, improsulfan tosilate, lomustine, melphalan, mitobronitol, mitolactol, nimustine, ranimustine, temozolomide, thiotepa, treosulfan, mechloretamine, carboquone, apaziquone, fotemustine, glufosfamide, palifosfamide, pipobroman, trofosfamide, uramustine;

Platinum Compounds
Such as carboplatin, cisplatin, eptaplatin, miriplatine hydrate, oxaliplatin, lobaplatin, nedaplatin, picoplatin, satraplatin;

DNA Altering Agents
Such as amrubicin, bisantrene, decitabine, mitoxantrone, procarbazine, trabectedin, clofarabine, amsacrin, brostallicin, pixantrone, laromustine;

Topoisomerase Inhibitors
Such as etoposide, irinotecan, razoxane, sobuzoxane, teniposide, topotecan, amonafide, belotecan, elliptinium acetate, voreloxin;

Microtubule Modifiers
Such as cabazitaxel, docetaxel, eribulin, ixabepilone, paclitaxel, vinblastine, vincristine, vinorelbine, vindesine, vinflunine, fosbretabulin, tesetaxel:

Antimetabolites
Such as asparaginase, azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur, doxifluridine, elacytarabine, raltitrexed, sapacitabine, tegafur, trimetrexate;

Anticancer Antibiotics

Such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin, aclarubicin, peplomycin, pirarubicin;

Hormones/Antagonists

Such as abarelix, abiraterone, bicalutamide, buserelin, calusterone, chlorotrianisene, degarelix, dexamethasone, estradiol, fluocortolone, fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol, acolbifene, danazol, deslorelin, epitiostanol, orteronel, enzalutamide;

Aromatase Inhibitors

Such as aminoglutethimide, anastrozole, exemestane, fadrozole, letrozole, testolactone, formestane;

Small Molecule Kinase Inhibitors

Such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib, afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib, cabozantinib S-malate, carfilzomib, ibrutinib, icotinib;

Photosensitizers

Such as Methoxsalen, porfimer sodium, talaporfin, temoporfin;

Antibodies

Such as alemtuzumab, besilesomab, brentuximab vedotin, cetuximab, denosumab, ipilimumab, ofatumumab, panitumumab, rituximab, tositumomab, trastuzumab, bevacizumab, catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab, onartuzumab, pertuzumab, racotumomab, tabalumab;

Cytokines

Such as aldesleukin, interferon alfa, interferon alfa2a, interferon alfa2b, tasonermin, teceleukin, oprelvekin;

Drug Conjugates

Such as denileukin diftitox, ibritumomab tiuxetan, iobenguane I123, prednimustine, trastuzumab emtansine, estramustine, gemtuzumab ozogamicin, aflibercept, cintredekin besudotox, edotreotide, inotuzumab ozogamicin, naptumomab estafenatox, oportuzumab monatox, technetium (99mTc) arcitumomab, vintafolide;

Vaccines

Such as sipuleucel, vitespen, emepepimut-S, oncoVAX, rindopepimut, troVax, stimuvax;

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel, sizofiran, tamibarotene, temsirolimus, thalidomide, tretinoin, vismodegib, zoledronic acid, thalidomide, vorinostat, celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine, picibanil, reolysin, retaspimycin hydrochloride, trebananib, virulizin.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating inflammatory, degenerative or hyperproliferative diseases for which compounds of the present invention are indicated, generally satisfactory results are obtained when the compounds of the present invention are administered at a daily dosage of from about 0.01 milligram to about 100 milligram per kilogram of body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

ABBREVIATIONS

Some abbreviations that may appear in this application are as follows:

| Designation | |
|---|---|
| API | Active Pharmaceutical Ingredient |
| DI | Deionized |
| DMF | Dimethylformamide |
| DMSO | Dimethyl Sulfoxide |
| DSC | Differential Scanning Calorimetry |
| FTIR | Fourier Transform Infrared Spectroscopy |
| h | Hour |
| HPLC | High Pressure Liquid Chromatography |
| M | Molar (unit of concentration) |
| MTBE | Methyl tertiary-butyl ether |
| N | Normal (unit of concentration) |
| NMP | N-methylpyrrolidone |
| PBS | Phosphate Buffered Saline |
| PTFE | Polytetrafluoroethylene |
| RT | Room Temperature (~23° C.) |
| TGA | Thermogravimetric Analysis |
| THF | Tetrahydrofurane |
| USP | U.S. Pharmacopeia |

EXAMPLES

The working examples presented below are intended to illustrate particular embodiments of the invention, and are not intended to limit the scope of the specification or the claims in any way.

By mono hydrochloride form is meant a stoichiometric ratio of Compound C to HCl between 0.8:1 and 1.2:1, preferably between 0.9:1 and 1.1:1. Most preferred is a ratio of 1:1.

1. Mono-Hydrochloride Form A1

1.1 Characterization of Form A1

1.1.1 X-Ray Powder Diffractometry

Figure 1:
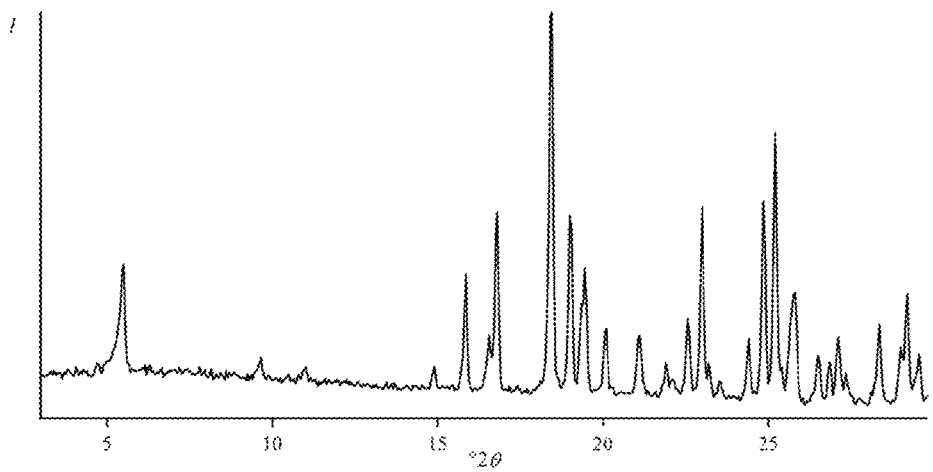
FIG. 1: Powder X-ray diffractogram of Form A1

A powder X-ray Diffraction pattern of Form A1 was obtained by standard techniques at RT as described in the European Pharmacopeia 6$^{th}$ Edition chapter 2.9.33, which is shown in FIG. 1.

A list of characteristic X-ray peaks derived from this pattern is provided in Table I:

| No. | °2θ (Cu-Kα₁ radiation) ± 0.2° |
|---|---|
| 1 | 5.5 |
| 2 | 15.9 |
| 3 | 16.8 |
| 4 | 18.5 |
| 5 | 19.1 |
| 6 | 19.5 |
| 7 | 20.1 |
| 8 | 21.1 |
| 9 | 22.6 |
| 10 | 23.0 |
| 11 | 24.4 |
| 12 | 24.9 |
| 13 | 25.2 |
| 14 | 25.7 |
| 15 | 27.1 |
| 16 | 28.4 |
| 17 | 29.2 |
| 18 | 29.6 |

The most significant X-ray peaks from Table I are listed in Table II:

| No. | °2θ (Cu-Kα₁ radiation) ± 0.2° |
|---|---|
| 1 | 5.5 |
| 2 | 16.8 |
| 3 | 18.5 |
| 4 | 19.1 |
| 5 | 22.6 |
| 6 | 23.0 |
| 7 | 24.9 |
| 8 | 25.2 |
| 9 | 28.4 |
| 10 | 29.2 |

Broken down by sample orientation, the most characteristic peaks are as listed in Tables III, IV and V:

TABLE III

| 0kl orientation | |
|---|---|
| No. | °2θ (Cu-Kα₁ radiation) ± 0.2° |
| 1 | 5.5 |
| 2 | 16.8 |
| 3 | 19.5 |
| 4 | 23.0 |

TABLE IV

| h0l orientation | |
|---|---|
| No. | °2θ (Cu-Kα₁ radiation) ± 0.2° |
| 1 | 5.5 |
| 2 | 18.5 |
| 3 | 19.1 |
| 4 | 28.4 |
| 5 | 29.6 |

TABLE V

| hk0 orientation | |
|---|---|
| No. | °2θ (Cu-Kα₁ radiation) ± 0.2° |
| 1 | 15.9 |
| 2 | 19.1 |
| 3 | 24.9 |

Therefore, in a preferred aspect the present invention relates to crystalline form A1 having characteristic peaks at the 2θ angles provided in Table I.

In a more preferred aspect the invention relates to form A1 having characteristic peaks at the 2θ angles provided in Table II.

In an equally preferred aspect the invention relates to form A1 having characteristic peaks at the 2θ angles provided in one or more of Tables III, IV and V.

1.1.2 X-Ray Singe Crystal Diffractometry

Figure 2:
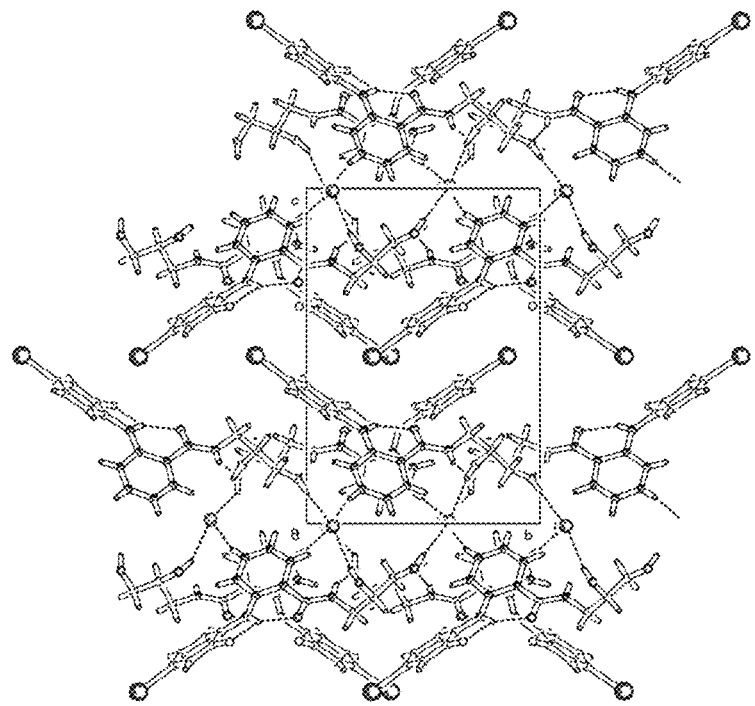
FIG. 2: Single crystal structure of Form A1

In addition, single crystal X-ray structure data were obtained on Form A1, from which the spacial arrangement of the A molecules in the crystal was computed as shown in FIG. 2.

Form A1 crystallises in the chiral monoclinic space group $P2_1$ with the lattice parameters a=9.6±0.1 Å, b=11.2±0.1 Å, c=16.6±0.1 Å, and β=104.4±0.5° ($\alpha=\gamma=90°$). From the single crystal structure it is obvious that Form A1 represents an anhydrous form.

In a specific aspect, the invention relates to a crystalline form of the mono hydrochloride of Compound C characterized by these crystallographic parameters.

1.1.3 Vibrational Spectroscopy

Form A1 can be further characterized by infrared and Raman-spectroscopy. FT-Raman and FT-IR spectra were obtained by standard techniques as described in the European Pharmacopeia $6^{th}$ Edition chapter 2.02.24 and 2.02.48. For measurement of the FT-IR and FT-Raman-spectra a Bruker Vector 22 and a Bruker RFS 100 spectrometer were used. FT-IR spectra and FT-Raman spectra were base-line corrected using Bruker OPUS software.

Figure 3:
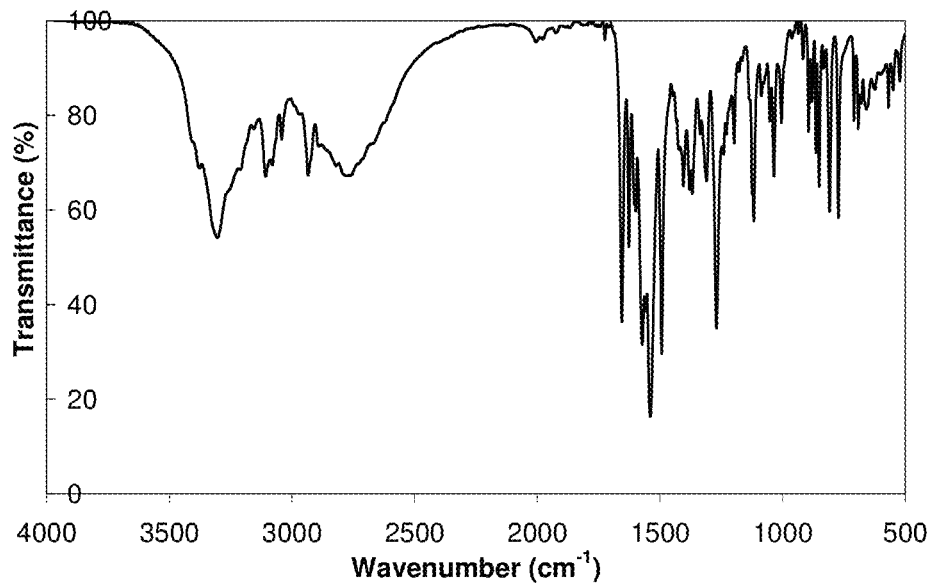
FIG. 3: FTIR spectrum of Form A1

An FT-IR spectrum was obtained using a KBr pellet as sample preparation technique. The FT-IR spectrum is shown in FIG. 3 from which band positions were derived as given below:

Form A1 IR band positions (±2 cm$^{-1}$, relative intensity*)
3108 cm$^{-1}$ (m), 2935 cm$^{-1}$ (m), 2772 cm$^{-1}$ (m), 1655 cm$^{-1}$ (s), 1539 cm$^{-1}$ (s), 1493 cm$^{-1}$ (s), 1380 cm$^{-1}$ (m), 1269 cm$^{-1}$ (s), 1118 cm$^{-1}$ (m), 1036 cm$^{-1}$ (m), 808 cm$^{-1}$ (m), 773 cm$^{-1}$ (m)

*"s"=strong (transmittance≤50%), "m"=medium (50%<transmittance≤70%), "w"=weak (transmittance>70%)

Figure 4:
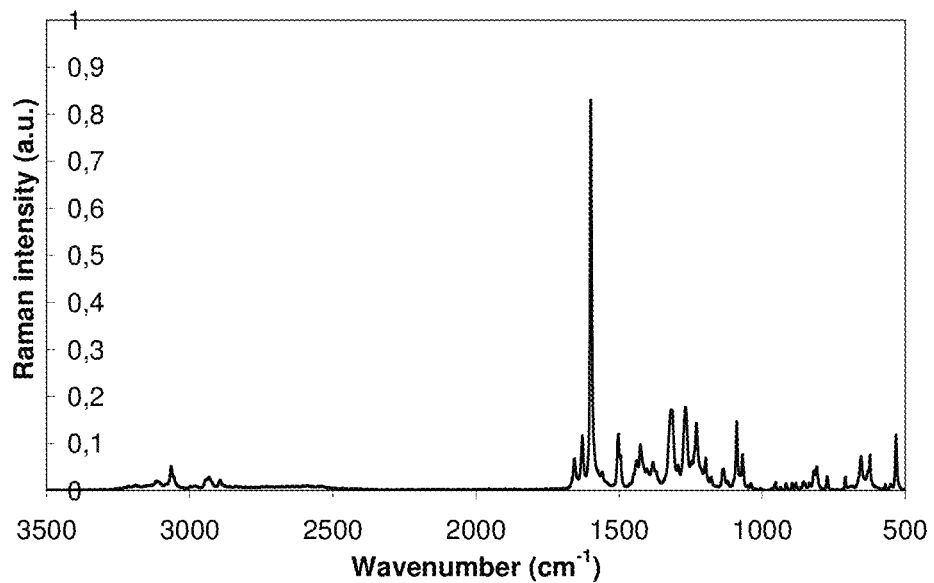
FIG. 4: FT Raman spectrum of Form A1

An FT-Raman spectrum is shown in FIG. 4 from which band positions were derived as given below:

Form A1 Raman band positions (±2 cm$^{-1}$, relative intensity*):
3065 cm$^{-1}$ (w), 1628 cm$^{-1}$ (m), 1599 cm$^{-1}$ (s), 1503 cm$^{-1}$ (m), 1319 cm$^{-1}$ (m), 1267 cm$^{-1}$ (m), 1230 cm$^{-1}$ (m), 1089 cm$^{-1}$ (m)

*"s"=strong (relative Raman intensity≥0.2), "m"=medium (0.2>relative Raman intensity≥0.1), "w"=weak (relative Raman intensity<0.1)

1.1.4 Other Analytical Methods

It could be shown that Form A1 is a crystalline anhydrous form, which is further characterised by the following physical properties:

Ion Chromatography revealed a chloride content of approx. 7.9 wt % Cl, which is equivalent to a molar acid:base ratio of 1.05:1.

Figure 5:
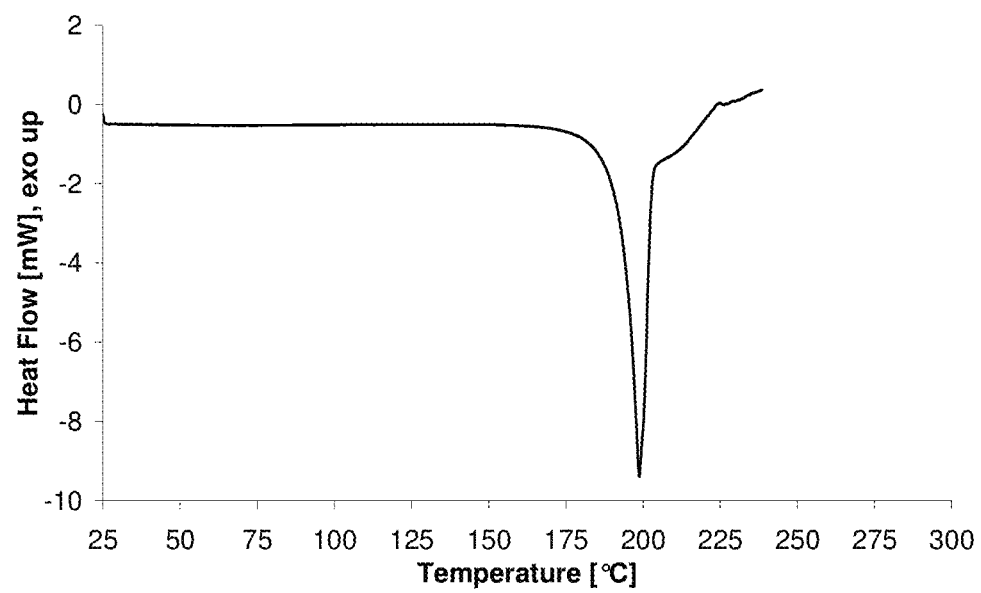
FIG. 5: DSC scan of Form A1
Figure 6:
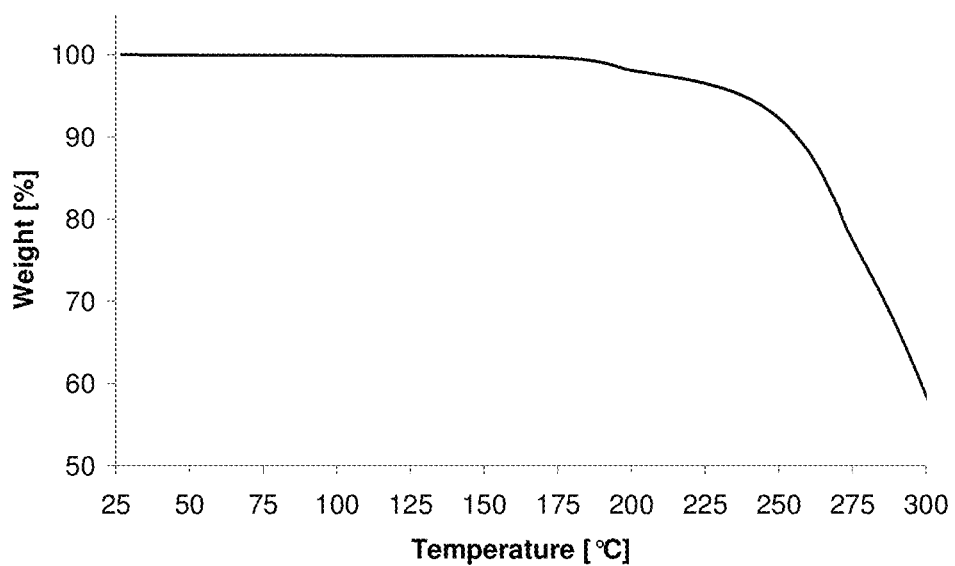
FIG. 6: TGA scan of Form A1

Thermal behaviour of Form A1 shows an overlapped melting/decomposition processes>160° C., with no significant weight loss up to this temperature. DSC and TGA profiles are shown in FIGS. 5 and 6. The DSC scan of Form A1 was acquired on a Mettler-Toledo DSC 821 with a heating rate of 5 K/min, using nitrogen purge gas at 50 mL/min. The TGA scan of Form A1 was acquired on a Perkin-Elmer Pyris TGA 1 with a heating rate of 5 K/min, using nitrogen purge gas at 50 mL/min.

Figure 7:
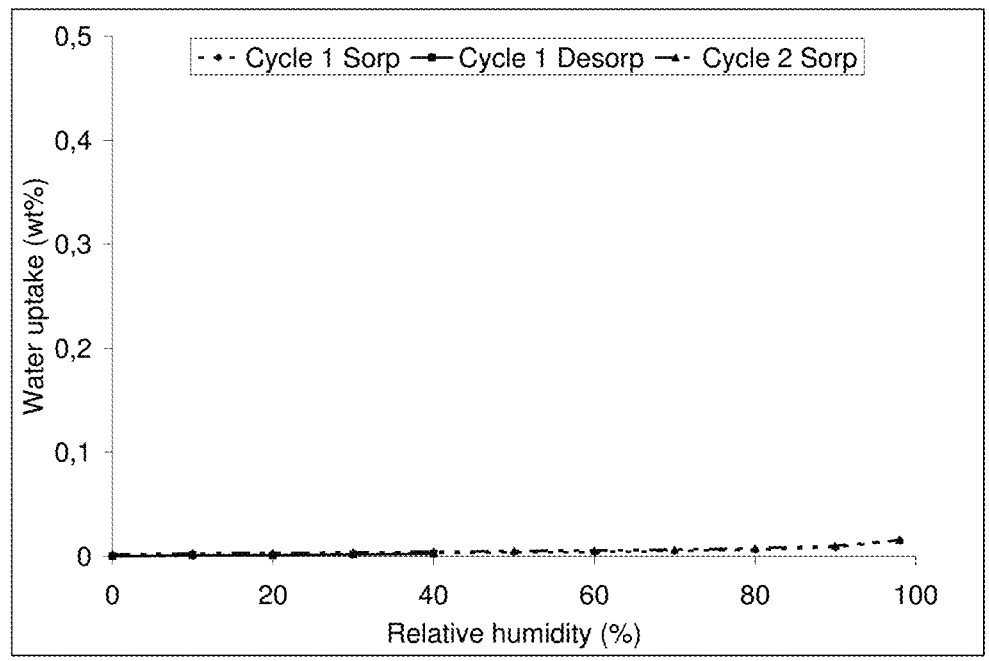
FIG. 7: Water Vapour Sorption Isotherm (25° C.) of Form A1

Water Vapour Sorption behaviour shows insignificant water uptake levels<0.1 wt % in the entire relative humidity range 0-98% RH. Form A1 can be classified as non-hygroscopic according to Ph. Eur. Criteria (section 5.11.). A Water Vapor Sorption isotherm (25° C.) of Form A1 is shown in FIG. 7, which was acquired on a DVS-1 System from SMS.

Solubility of Form A1 in DI Water at 37° C. was determined to be approx. 2.8 mg/mL, solubility of Form A1 at 37° C. in 0.1. N HCl at 37° C. was determined to be approx. 44 mg/mL (see Example 9).

Active Pharmaceutical Ingredient dissolution studies with Form A1 in various buffer systems at 37° C. revealed rapid and complete dissolution in the pH range 1.2 to 6.8 (see Example 10).

Overall, Form A1 reveals very good solid-state properties (very good crystallinity, non-hygroscopic, sufficient thermal stability) with significantly improved aqueous solubility compared to the free base (see Example 9).

1.2 Processes for the Preparation of A1

General reaction scheme to obtain acetonide-protected C:

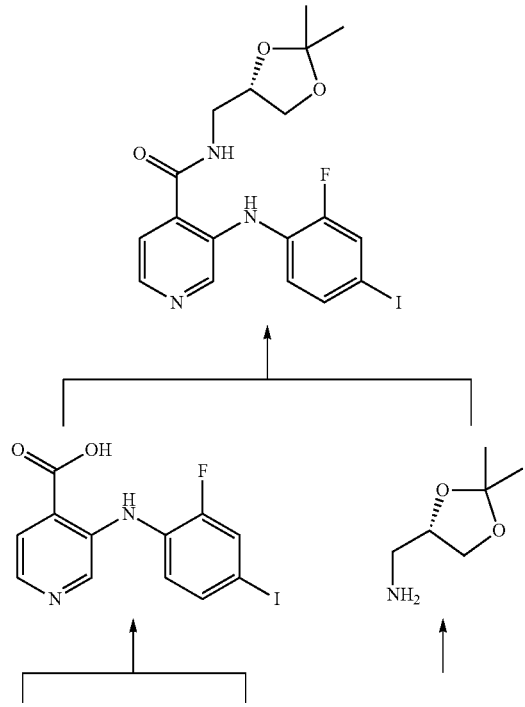

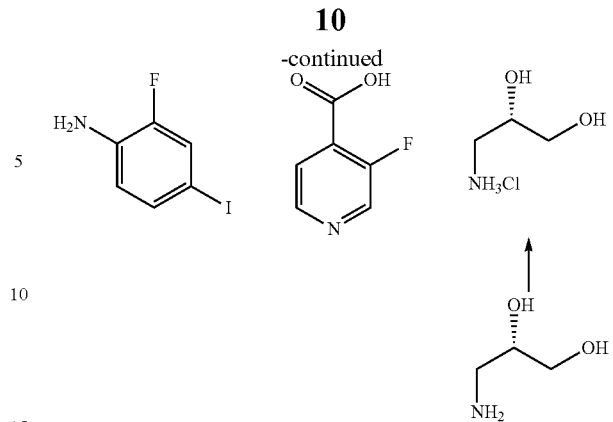

Reaction scheme to obtain HCl salt Form A1 from acetonide-protected C:

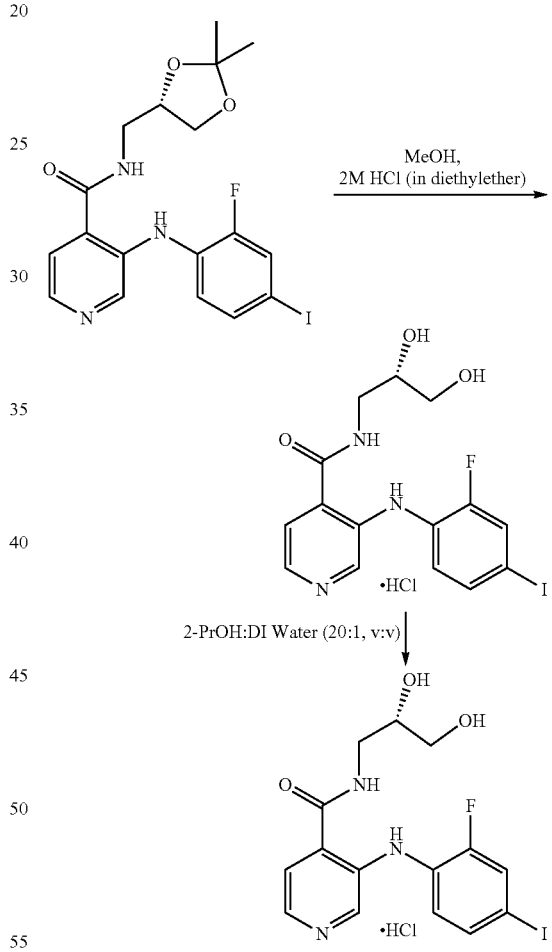

1.2.1 Method 1

A solution of acetonide-protected Compound C as free base (1.0 wt) in methanol (20.0 vol) was clarified through a 0.7 μm glass microfibre filter paper. Clarified ca. 2 M hydrochloric acid in diethyl ether (5.3 vol) was added to the methanolic solution at 16 to 25° C. The mixture was stirred for 60 to 90 minutes at 16 to 25° C. and filtered. The filter-cake was washed with a clarified mixture of methanol/diethyl ether 4:1 (1.0 vol) and pulled dry on the pad for 60 to 90 minutes. The filter-cake was transferred to a suitable vessel and clarified propan-2-ol (20.0 vol) and clarified water (1.0 vol) was charged. The mixture was heated to and stirred at 75 to 85° C. for 30 to 50 minutes. The mixture was cooled to 0 to 5° C. over 60 to 90 minutes and aged at 0 to 5° C. for 20 to 30 minutes and filtered. The filter-cake was washed with clarified propan-2-ol (1.0 vol) and pulled dry on the filter under nitrogen for up to 24 hours to give a pre-blend of Compound C hydrochloride. A mixture of the pre-blend Form A1 (1.0 wt %) and propan-2-ol (3.0 vol) was charged to a suitable flask and stirred for 60 to 90 minutes at 16 to 25° C. The mixture was filtered and the filter-cake was washed with propan-2-ol (1.0 vol) and pulled dry on the filter under nitrogen for up to 24 hours.

The filter-cake was transferred to drying trays and dried under vacuum at up to 40° C. until the propan-2-ol content was 0.2 wt % to give Form A1.

1.2.2 Method 2

Approx. 800 g of Form A2 (see Example 2) were dispersed in 16 L 2-Propanol and 0.8 L Water, and heated to 80° C. The reaction mixture was kept at 80° C. for 3 hours, and slowly cooled down to room temperature. The dispersion was then kept at room temperature for 3 hours, and then further cooled down to 0° C. The dispersion was then filtered, and the obtained filter residue was dried at 40° C. under vacuum overnight.

1.2.3 Method 3

Approx. 25 mg of Compound C mono hydrochloride were dispersed in 0.3 mL DMF, and heated to 50° C. The resulting solution was then cooled to RT in approx. 1 h, resulting in yellow crystals.

2. Mono-Hydrochloride Form A2

2.1 Characterization of Form A2

2.1.1 X-Ray Powder Diffractometry

Figure 8:
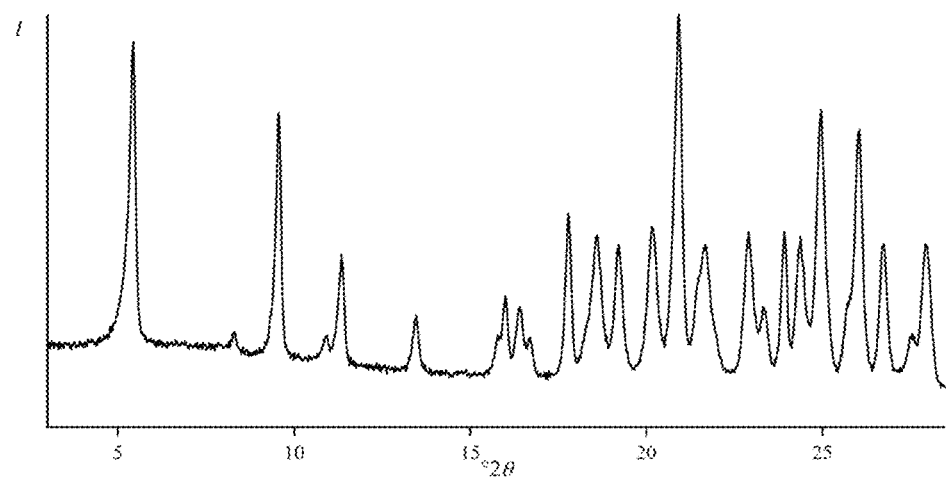
FIG. 8: Powder X-ray diffractogram of Form A2

A Powder X-Ray Diffraction pattern of Form A2 was obtained by standard techniques at RT as described in the European Pharmacopeia 6$^{th}$ Edition chapter 2.9.33, which is shown in FIG. 8.

A list of characteristic X-ray peaks derived from this pattern is provided in Table VI:

| No. | °2θ (Cu-Kα$_1$ radiation) ± 0.2° |
|---|---|
| 1 | 5.4 |
| 2 | 9.6 |
| 3 | 11.3 |
| 4 | 13.5 |
| 5 | 16.0 |
| 6 | 16.4 |
| 7 | 16.7 |
| 8 | 17.8 |
| 9 | 18.4 |
| 10 | 18.6 |
| 11 | 19.2 |
| 12 | 20.2 |
| 13 | 20.9 |
| 14 | 21.6 |
| 15 | 22.9 |
| 16 | 23.3 |
| 17 | 23.9 |
| 18 | 24.4 |
| 19 | 25.0 |
| 20 | 26.0 |
| 21 | 26.7 |
| 22 | 27.5 |
| 23 | 27.9 |

The most significant X-ray peaks from Table VI are listed in Table VII:

| No. | °2θ (Cu-Kα$_1$ radiation) ± 0.2° |
|---|---|
| 1 | 5.4 |
| 2 | 9.6 |
| 3 | 18.4 |
| 4 | 18.6 |
| 5 | 20.9 |
| 6 | 21.6 |
| 7 | 23.9 |
| 8 | 24.4 |
| 9 | 25.0 |
| 10 | 26.0 |

Broken down by sample orientation, the most characteristic peaks are as listed in Tables VIII, and IX:

TABLE VIII h0l orientation

| No. | °2θ (Cu-Kα$_1$ radiation) ± 0.2° |
|---|---|
| 1 | 18.4 |
| 2 | 18.6 |
| 3 | 19.2 |
| 4 | 20.2 |
| 5 | 21.6 |

TABLE IX hk0 orientation

| No. | °2θ (Cu-Kα$_1$ radiation) ± 0.2° |
|---|---|
| 1 | 9.6 |
| 2 | 11.3 |
| 3 | 17.8 |
| 4 | 23.9 |
| 5 | 25.0 |

Therefore, in a preferred aspect the present invention relates to crystalline form A2 having characteristic peaks at the 2θ angles provided in Table VI.

In a more preferred aspect the invention relates to form A2 having characteristic peaks at the 2θ angles provided in Table VII.

In an equally preferred aspect the invention relates to form A1 having characteristic peaks at the 2θ angles provided in one or more of Tables VIII and IX.

Figure 9:
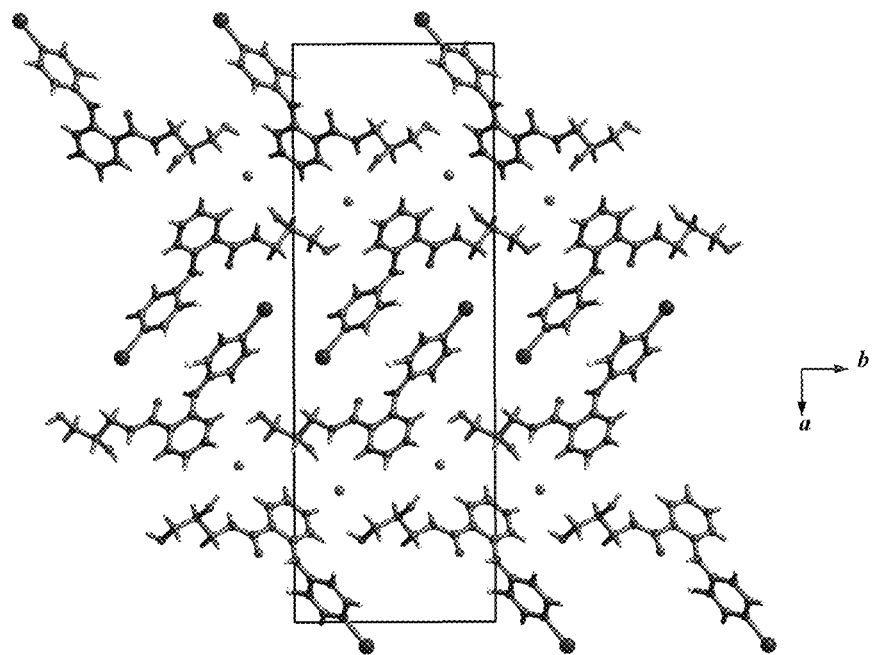
FIG. 9: Crystal structure of Form A2 (calculated from Powder data)

X-ray structural data were calculated from powder X-ray data of Form A2 as shown in FIG. 9.

Form A2 crystallises in the chiral orthorhombic space group P2$_1$2$_1$2 with the lattice parameters (measured at 301 K) a=32.3±0.1 Å, b=11.2±0.1 Å, c=4.8±0.1 Å (α=β=γ=90°). From the crystal structure it is obvious that Form A2 represents an anhydrous form.

In a specific aspect, the invention relates to a crystalline form of the mono hydrochloride of Compound C characterized by these crystallographic parameters.

2.1.2 Vibrational Spectroscopy

Form A2 can be further characterized by infrared and Raman-spectroscopy. FT-Raman and FT-IR spectra were obtained by standard techniques as described in the European Pharmacopeia 6$^{th}$ Edition chapter 2.02.24 and 2.02.48. For measurement of the FT-IR and FT-Raman-spectra a Bruker Vector 22 and a Bruker RFS 100 spectrometer were used. FT-IR spectra were base-line corrected using Bruker OPUS software. FT-Raman spectra were vector normalized using the same software.

Figure 10:
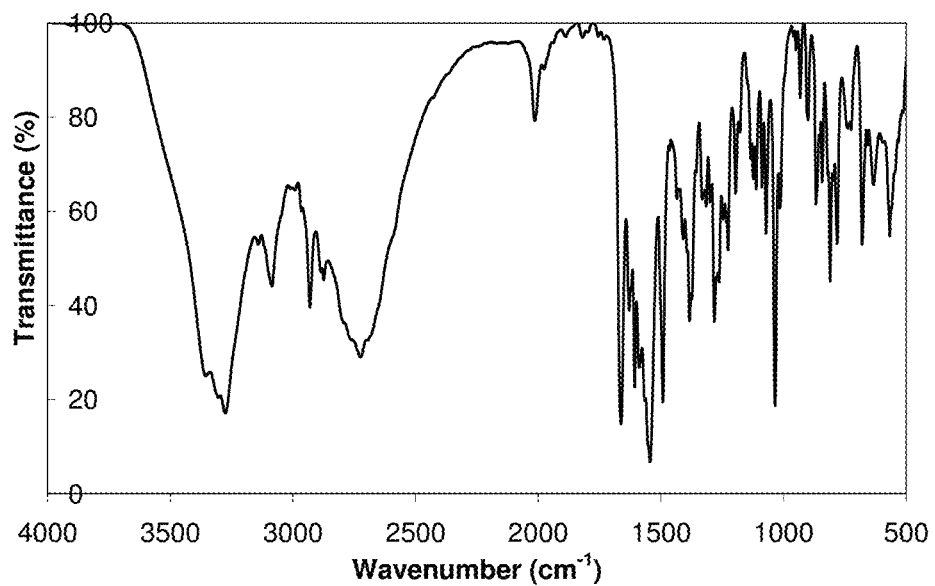
FIG. 10: FTIR spectrum of Form A2

An FT-IR spectrum was obtained using a KBr pellet as sample preparation technique. The FT-IR spectrum is shown in FIG. 10 from which band positions were derived as given below.

Form A2 IR band positions (±2 cm$^{-1}$, relative intensity*)

3086 cm$^{-1}$ (s), 2931 cm$^{-1}$ (s), 2724 cm$^{-1}$ (s), 1663 cm$^{-1}$ (s), 1544 cm$^{-1}$ (s), 1492 cm$^{-1}$ (s), 1383 cm$^{-1}$ (s), 1282 cm$^{-1}$ (s), 1035 cm$^{-1}$ (s), 810 cm$^{-1}$ (s), 782 cm$^{-1}$ (m)

*"s"=strong (transmittance≤50%), "m"=medium (50%<transmittance≤70%), "w"=weak (transmittance>70%)

Figure 11:
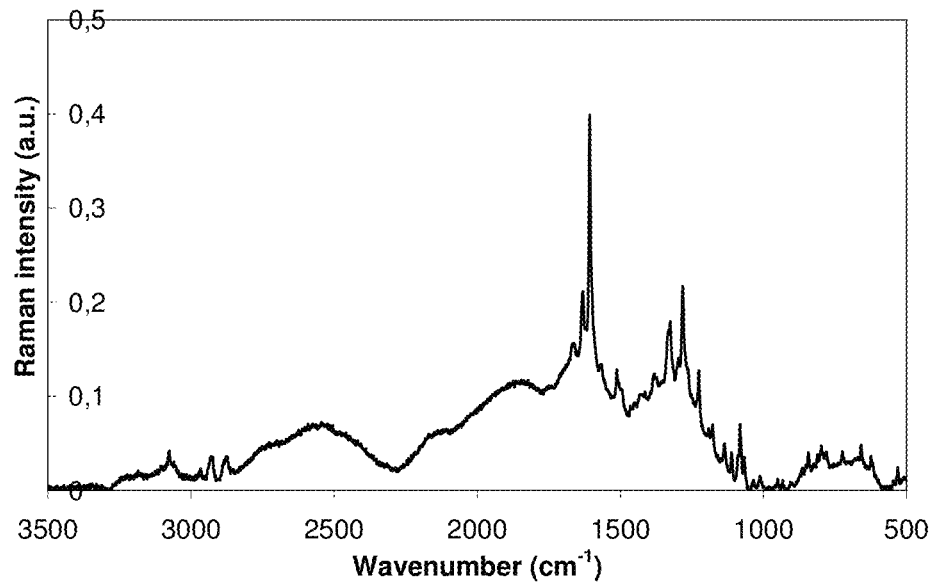
FIG. 11: FT Raman spectrum of Form A2

An FT-Raman spectrum is shown in FIG. 11 from which band positions were derived as given below:

Form A2 Raman band positions (±2 cm$^{-1}$, relative intensity*):

3077 cm$^{-1}$ (w), 1631 cm$^{-1}$ (s), 1607 cm$^{-1}$ (s), 1513 cm$^{-1}$ (m), 1326 cm$^{-1}$ (m), 1282 cm$^{-1}$ (s), 1226 cm$^{-1}$ (m), 1082 cm$^{-1}$ (w)

*"s"=strong (relative Raman intensity≥0.2), "m"=medium (0.2>relative Raman intensity≥0.1), "w"=weak (relative Raman intensity<0.1)

2.1.3 Other Analytical Methods

It could be shown that Form A2 is a crystalline anhydrous form, which is further characterised by the following physical properties:

Ion Chromatography revealed a chloride content of approx. 7.8 wt % Cl, which is equivalent to a molar acid:base ratio of 1.03:1

Figure 12:
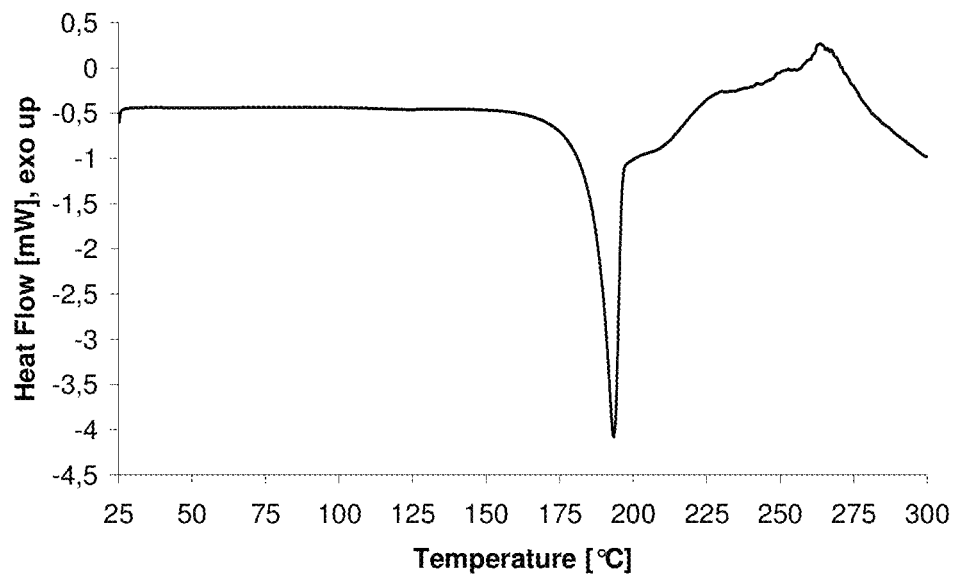
FIG. 12: DSC scan of Form A2
Figure 13:
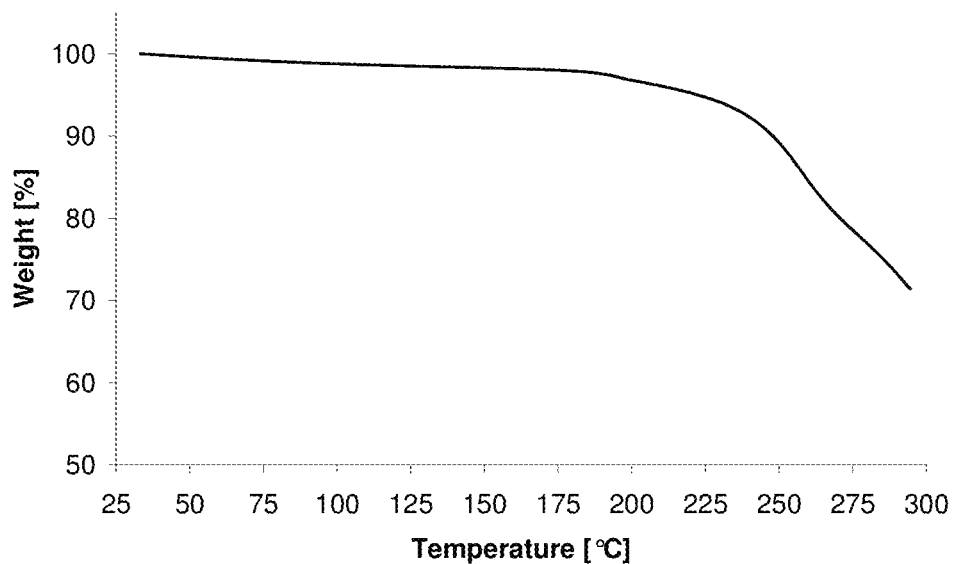
FIG. 13: TGA scan of Form A2

Thermal behaviour of Form A2 shows an overlapped melting/decomposition processes>160° C., with no significant weight loss up to this temperature. DSC and TGA profiles are shown in FIGS. 12 and 13. The DSC scan of Form A2 was acquired on a Mettler-Toledo DSC 821 with a heating rate of 5 K/min, using nitrogen purge gas at 50 mL/min. The TGA scan of Form A2 was acquired on a Mettler-Toledo TGA 851 with a heating rate of 5 K/min, using nitrogen purge gas at 50 mL/min.

Figure 14:
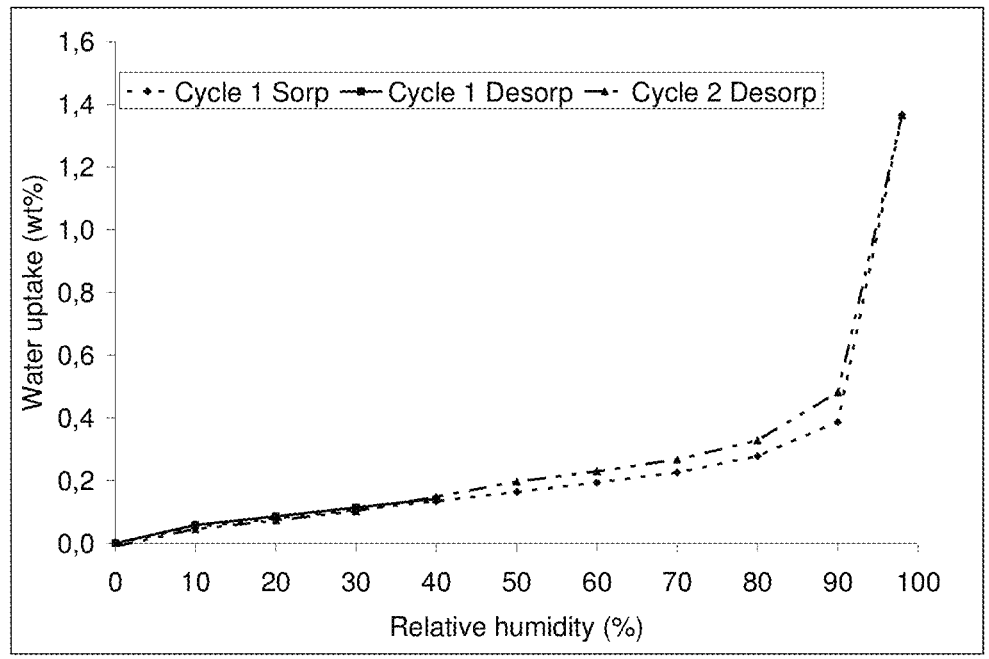
FIG. 14: Water Vapour Sorption Isotherm (25° C.) of Form A2

Water Vapour Sorption behaviour shows small water uptake levels only, with a fully reversible adsorption/desorption behaviour. Form A2 can be classified as slightly hygroscopic acc. to Ph. Eur. Criteria (section 5.11.). A Water Vapor Sorption isotherm (25° C.) of Form A2 is shown in FIG. 14, which was acquired on a DVS-1 System from SMS.

Solubility of Form A2 in DI Water at 37° C. was determined to be approx. 2.5 mg/mL, solubility of Form A2 at 37° C. in 0.1. N HCl at 37° C. was determined to >20 mg/mL (see Example 9).

Active Pharmaceutical Ingredient dissolution studies with Form A2 in various buffer systems at 37° C. revealed rapid and complete dissolution in the pH range 1.2 to 6.8 (see Example 10).

Overall, Form A2 reveals good solid-state properties (good crystallinity, slightly hygroscopic, sufficient thermal stability) with significantly improved aqueous solubility compared to the free base (see Example 9).

2.2 Processes for the Preparation of A2

Reaction scheme to obtain HCl salt Form A2 from acetonide-protected A:

2.2.1 Method 1

Approx. 350 g of acetonide-protected Compound C as free base were dispersed in 7 L dry methanol, and approx. 1.86 L 2 N HCl solution (in diethylether) was added. From the resulting solution a yellow solid precipitated. The reaction mixture was stirred for approx. 4 hours until complete reaction was observed. The dispersion was filtered, washed with diethyl ether, and dried under vacuum for 24 hours.

2.2.2 Method 2

Approx. 145 mg of acetonide-protected Compound C as free base were dispersed in 1.5 mL methanol at RT, and approx. 1.5 mL 1.25 N HCl solution (in methanol) was added at RT. From the resulting solution a yellow solid precipitated. The reaction mixture was stirred for approx. 14 hours before 2 mL of MTBE were added. The dispersion was filtered, washed with MTBE, and dried under vacuum at 40° C. for 4 hours.

2.2.3 Method 3

Approx. 145 mg of acetonide-protected Compound C as free base were dispersed in 1.5 mL methanol at RT, and approx. 1.5 mL 1.25 N HCl solution (in methanol) was added at RT. From the resulting solution a yellow solid precipitated. The reaction mixture was stirred for approx. 6 hours before 2 mL of 2-Propanol were added. The dispersion was filtered, washed with 2-Propanol, and dried under vacuum at 40° C.

2.2.4 Method 4

Approx. 45 mg of Compound C mono hydrochloride were dissolved in 0.5 mL DMSO. The solvent was allowed to evaporate completely at RT, resulting in yellow-orange crystals.

3. Solvates of Compound C Mono Hydrochloride

In addition to Forms A1 and A2 described above a series of solvate forms of C mono hydrochloride were also identified, the physical properties of which were not further characterized.

3.1 Dioxane Solvate Form A-NF3

Figure 15:
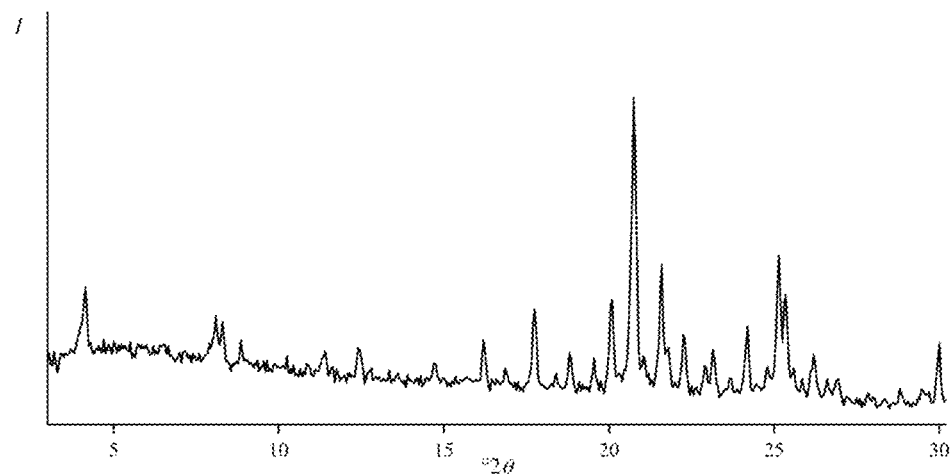
FIG. 15: Powder X-ray diffractogram of Form A-NF3

From the powder X-ray diffractogram of Form NF3 shown in FIG. 15 the following peaks were derived—Table X:

| No. | °2θ (Cu-Kα₁ radiation) ± 0.2° |
|---|---|
| 1 | 4.2 |
| 2 | 8.1 |
| 3 | 14.7 |
| 4 | 16.2 |
| 5 | 17.8 |
| 6 | 18.8 |
| 7 | 19.6 |
| 8 | 20.1 |
| 9 | 20.8 |
| 10 | 21.6 |
| 11 | 22.3 |
| 12 | 22.9 |
| 13 | 23.2 |
| 14 | 24.2 |
| 15 | 25.2 |
| 16 | 25.4 |
| 17 | 30.0 |

3.2 Acetic Acid Solvate Form A-NF6

Figure 16:
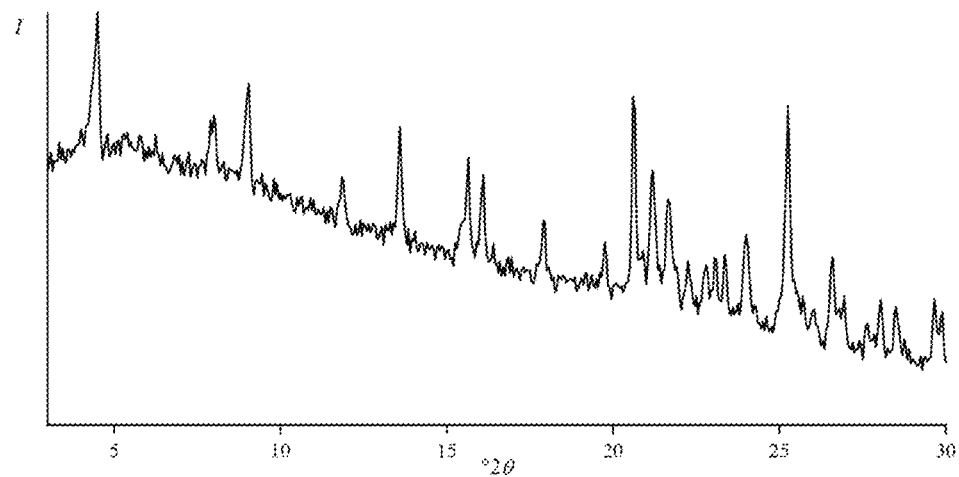
FIG. 16: Powder X-ray diffractogram of Form A-NF6

From the powder X-ray diffractogram of Form A-NF6 shown in FIG. 16 the following peaks were derived—Table XI:

| No. | °2θ (Cu-Kα₁ radiation) ± 0.2° |
|---|---|
| 1 | 4.5 |
| 2 | 8.0 |
| 3 | 9.0 |
| 4 | 13.6 |
| 5 | 15.7 |
| 6 | 16.1 |
| 7 | 18.0 |
| 8 | 20.6 |
| 9 | 21.2 |
| 10 | 21.7 |
| 11 | 24.0 |
| 12 | 25.3 |
| 13 | 26.6 |
| 14 | 28.1 |
| 15 | 28.5 |
| 16 | 29.7 |
| 17 | 29.9 |

3.3 NMP Solvate Form A-NF9

Figure 17:
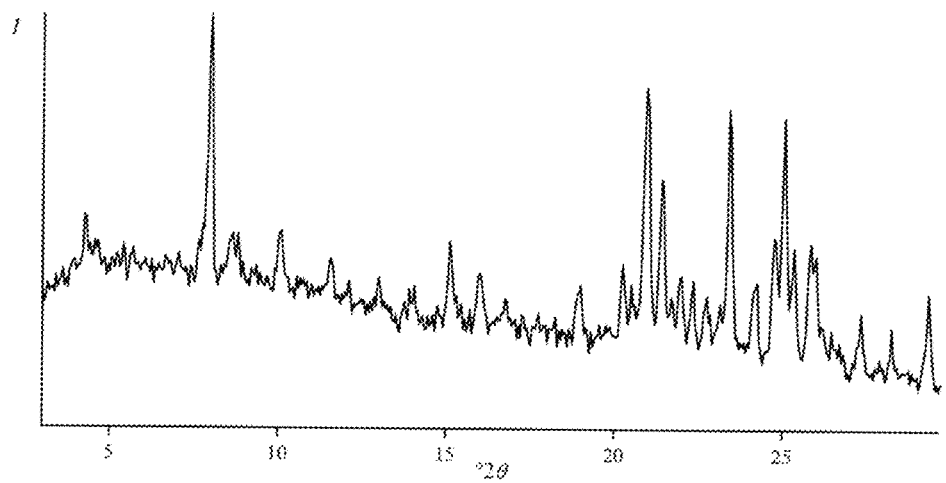
FIG. 17: Powder X-ray diffractogram of Form A-NF9

From the powder X-ray diffractogram of Form A-NF9 shown in FIG. 17 the following peaks were derived—Table XII:

| No. | °2θ (Cu-Kα₁ radiation) ± 0.2° |
|---|---|
| 1 | 4.3 |
| 2 | 8.0 |
| 3 | 8.6 |
| 4 | 10.1 |
| 5 | 11.6 |
| 6 | 15.1 |
| 7 | 16.0 |
| 8 | 19.0 |
| 9 | 20.3 |
| 10 | 21.0 |
| 11 | 21.5 |
| 12 | 23.4 |
| 13 | 24.2 |
| 14 | 24.8 |
| 15 | 25.1 |
| 16 | 25.4 |
| 17 | 25.9 |
| 18 | 27.4 |
| 19 | 29.4 |

3.4 NMP Solvate Form A-NF10

Figure 18:
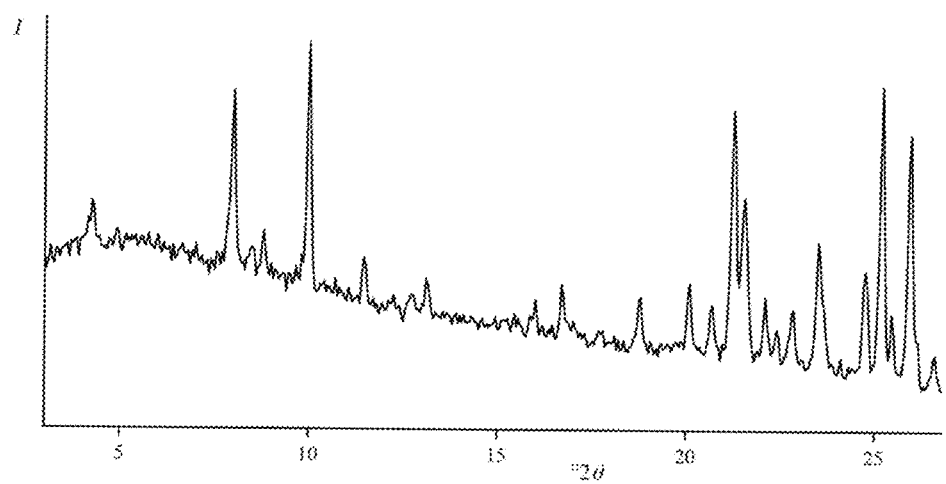
FIG. 18: Powder X-ray diffractogram of Form A-NF10

From the powder X-ray diffractogram of Form A-NF10 shown in FIG. 18 the following peaks were derived—Table XIII:

| No. | °2θ (Cu-Kα₁ radiation) ± 0.2° |
|---|---|
| 1 | 4.3 |
| 2 | 8.0 |
| 3 | 10.0 |
| 4 | 16.7 |
| 5 | 18.8 |
| 6 | 20.1 |
| 7 | 20.7 |
| 8 | 21.2 |
| 9 | 21.6 |
| 10 | 22.1 |
| 11 | 22.9 |
| 12 | 23.5 |
| 13 | 24.8 |
| 14 | 25.2 |
| 15 | 25.5 |
| 16 | 26.0 |
| 17 | 26.6 |

3.5 NMP Solvate Form A-NF11

Figure 19:
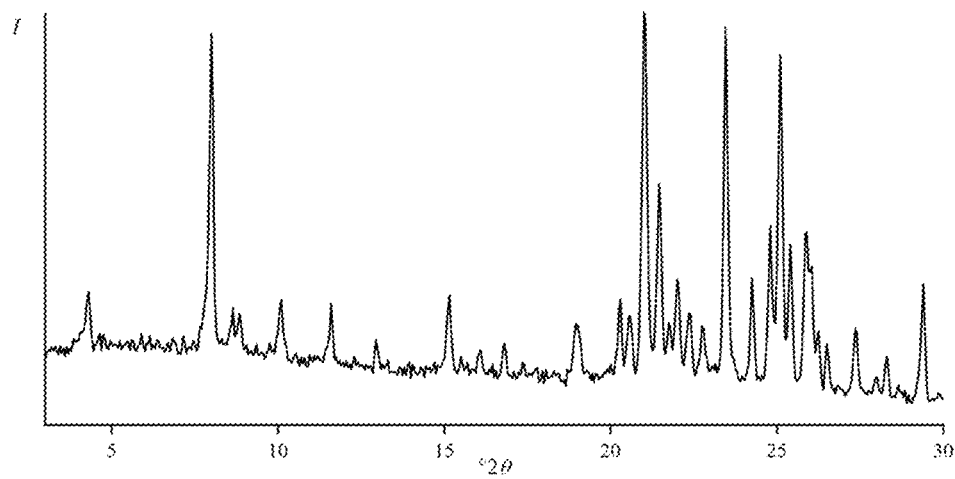
FIG. 19: Powder X-ray diffractogram of Form A-NF11

From the powder X-ray diffractogram of Form A-NF11 shown in FIG. 19 the following peaks were derived—Table XIV:

| No. | °2θ (Cu-Kα₁ radiation) ± 0.2° |
|---|---|
| 1 | 4.3 |
| 2 | 8.0 |
| 3 | 10.1 |
| 4 | 11.6 |
| 5 | 15.2 |
| 6 | 19.0 |
| 7 | 20.3 |
| 8 | 20.6 |
| 9 | 21.0 |
| 10 | 21.5 |
| 11 | 22.0 |
| 12 | 22.4 |
| 13 | 23.5 |
| 14 | 24.3 |
| 15 | 24.8 |
| 16 | 25.1 |
| 17 | 25.4 |
| 18 | 25.9 |
| 19 | 27.4 |
| 20 | 29.4 |

4. Free Base Form B1

4.1 Characterization of Form B1

4.1.1 X-Ray Powder Diffractometry

Figure 20:
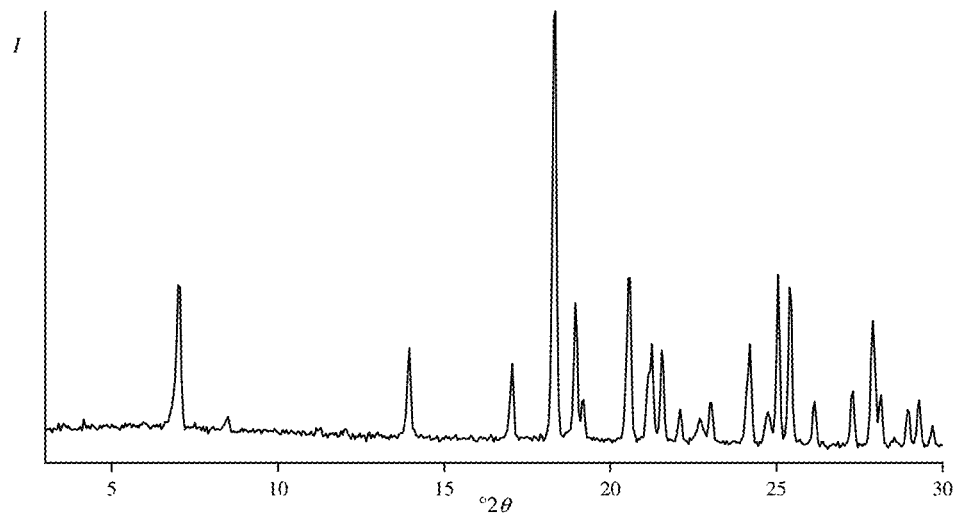
FIG. 20: Powder X-ray diffractogram of Form B1

A Powder X-Ray Diffraction pattern of Form B1 was obtained by standard techniques at 301 K as described in the European Pharmacopeia 6$^{th}$ Edition chapter 2.9.33, which is shown in FIG. 20.

A list of characteristic X-ray peaks derived from this pattern is provided in Table XV:

| No. | °2θ (Cu-Kα₁ radiation) ± 0.2° |
|---|---|
| 1 | 7.0 |
| 2 | 14.0 |
| 3 | 17.1 |
| 4 | 18.3 |
| 5 | 19.0 |
| 6 | 19.2 |
| 7 | 20.6 |
| 8 | 21.2 |

-continued

| No. | °2θ (Cu-Kα$_1$ radiation) ± 0.2° |
|---|---|
| 9 | 21.6 |
| 10 | 22.1 |
| 11 | 23.1 |
| 12 | 24.2 |
| 13 | 25.1 |
| 14 | 25.4 |
| 15 | 26.2 |
| 16 | 27.3 |
| 17 | 27.9 |
| 18 | 29.0 |
| 19 | 29.3 |

The most significant X-ray peaks from Table X are listed in Table XVI:

| No. | °2θ (Cu-Kα$_1$ radiation) ± 0.2° |
|---|---|
| 1 | 7.0 |
| 2 | 14.0 |
| 3 | 18.3 |
| 4 | 19.0 |
| 5 | 20.6 |
| 6 | 21.2 |
| 7 | 24.2 |
| 8 | 25.1 |
| 9 | 25.4 |
| 10 | 27.9 |

Therefore, in a preferred aspect the present invention relates to crystalline form B1 having characteristic peaks at the 2θ angles provided in Table XV.

In a more preferred aspect the invention relates to form B1 having characteristic peaks at the 2θ angles provided in Table XVI.

Figure 21:
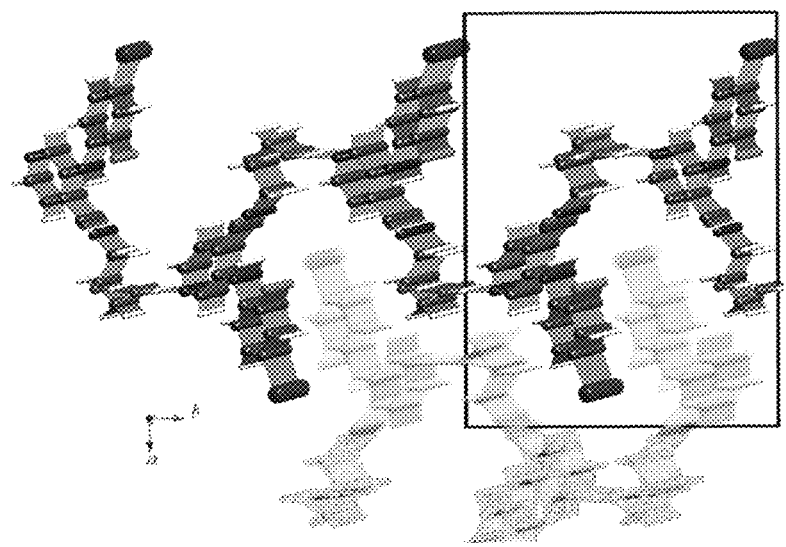
FIG. 21: Crystal structure of Form B1 (calculated from Powder data)

X-Ray Structural data were calculated from powder X-Ray data of Form B1 as shown in FIG. 21.

Form B1 crystallises in the chiral orthorhombic space group P2$_1$2$_1$2$_1$ with the lattice parameters a=20.8±0.1 Å, b=15.7±0.1 Å, c=5.0±0.1 Å α=β=γ=90°) at 301 K. From the crystal structure it is obvious that Form B1 represents an anhydrous form.

In a specific aspect, the invention relates to a crystalline form of the free base of Compound C characterized by these crystallographic parameters.

4.1.2 Vibrational Spectroscopy

Form B1 can be further characterized by infrared and Raman-spectroscopy. FT-Raman and FT-IR spectra have been obtained by standard techniques as described in the European Pharmacopeia 6$^{th}$ Edition chapter 2.02.24 and 2.02.48. For measurement of the FT-IR and FT-Raman-spectra a Bruker Vector 22 and a Bruker RFS 100 spectrometer have been used. FT-IR spectra and FT-Raman spectra have been base-line corrected using Bruker OPUS software.

Figure 22:
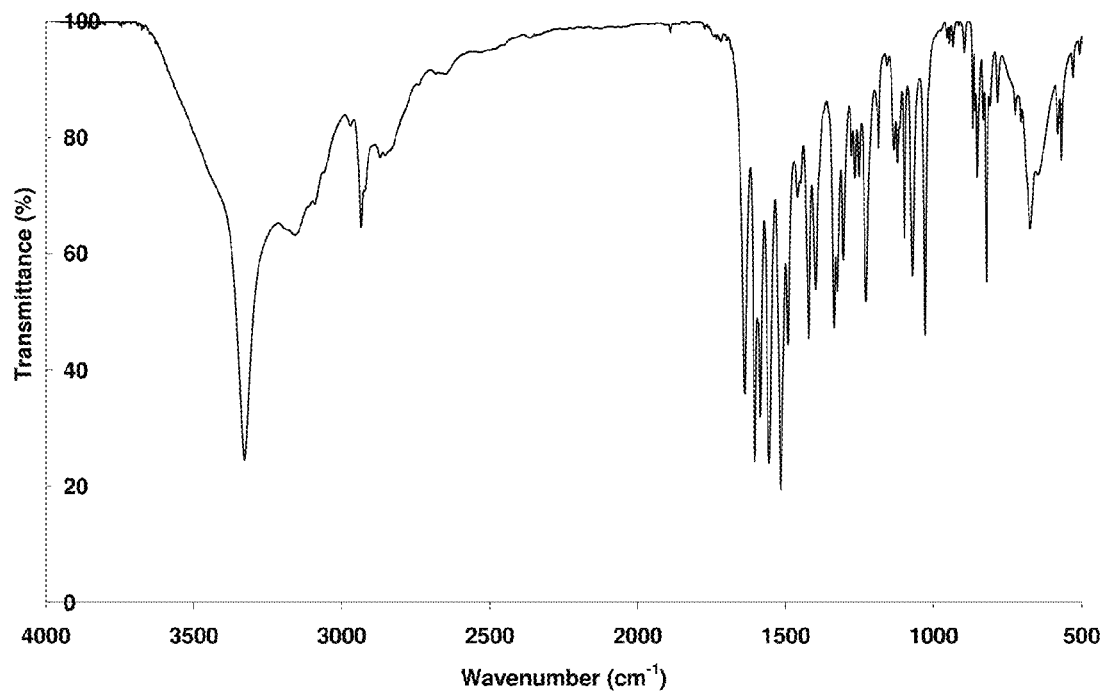
FIG. 22: FTIR spectrum of Form B1

An FT-IR spectrum has been obtained using a KBr pellet as sample preparation technique. The FT-IR spectrum is shown in FIG. 22 from which the following band positions were derived (±2 cm$^{-1}$, relative intensity*):

3329 cm$^{-1}$ (s), 2935 cm$^{-1}$ (w), 1638 cm$^{-1}$ (s), 1604 cm$^{-1}$ (s), 1585 cm$^{-1}$ (s), 1555 cm$^{-1}$ (s), 1516 cm$^{-1}$ (s), 1422 cm$^{-1}$ (s), 1398 cm$^{-1}$ (m), 1337 cm$^{-1}$ (s), 1228 cm$^{-1}$ (m), 1098 cm$^{-1}$ (m), 1071 cm$^{-1}$ (m), 1028 cm$^{-1}$ (s)

*"s"=strong (transmittance≤50%), "m"=medium (50%<transmittance≤70%), "w"=weak (transmittance>70%)

Figure 23:
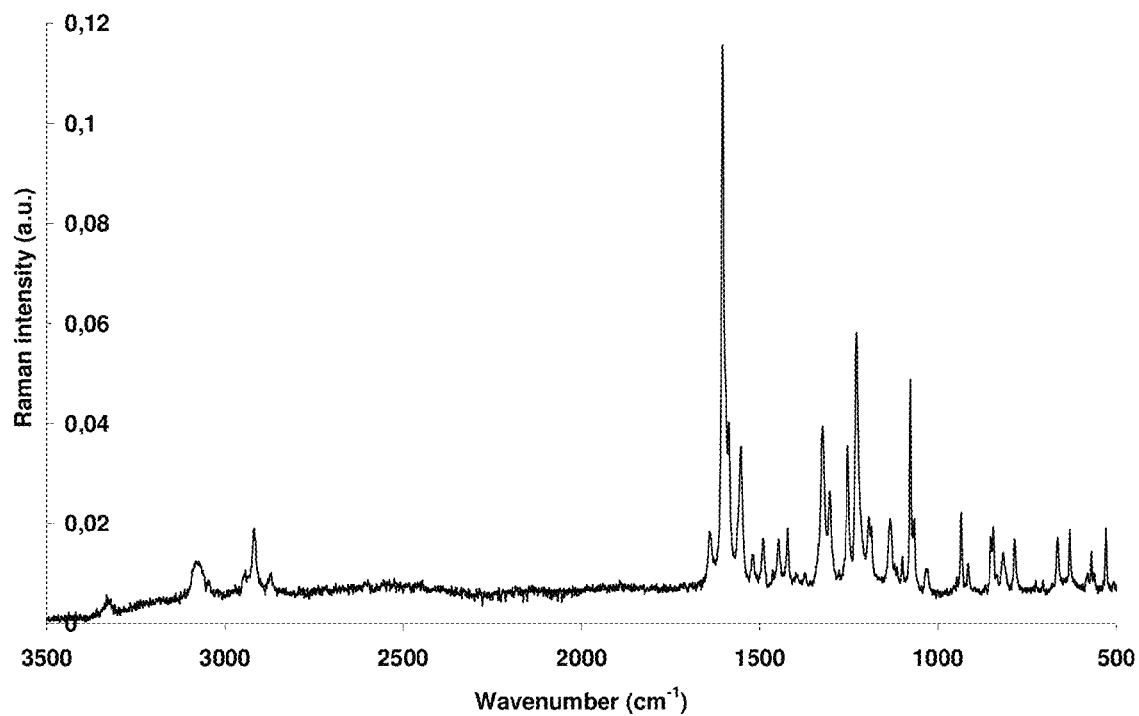
FIG. 23: FT Raman spectrum of Form B1

An FT-Raman spectrum is shown in FIG. 23 from which the following band positions were derived (±2 cm$^{-1}$, relative intensity*):

3081 cm$^{-1}$ (w), 2918 cm$^{-1}$ (w), 1604 cm$^{-1}$ (s), 1553 cm$^{-1}$ (m), 1323 cm$^{-1}$ (m), 1253 cm$^{-1}$ (m), 1228 cm$^{-1}$ (m), 1134 cm$^{-1}$ (w), 1077 cm$^{-1}$ (m), 935 cm$^{-1}$ (w), 785 cm$^{-1}$ (w), 630 cm$^{-1}$ (w), 529 cm$^{-1}$ (w)

*"s"=strong (relative Raman intensity≥0.1), "m"=medium (0.1>relative Raman intensity≥0.02), "w"=weak (relative Raman intensity<0.02)

4.1.3 Other Analytical Methods

Figure 24:
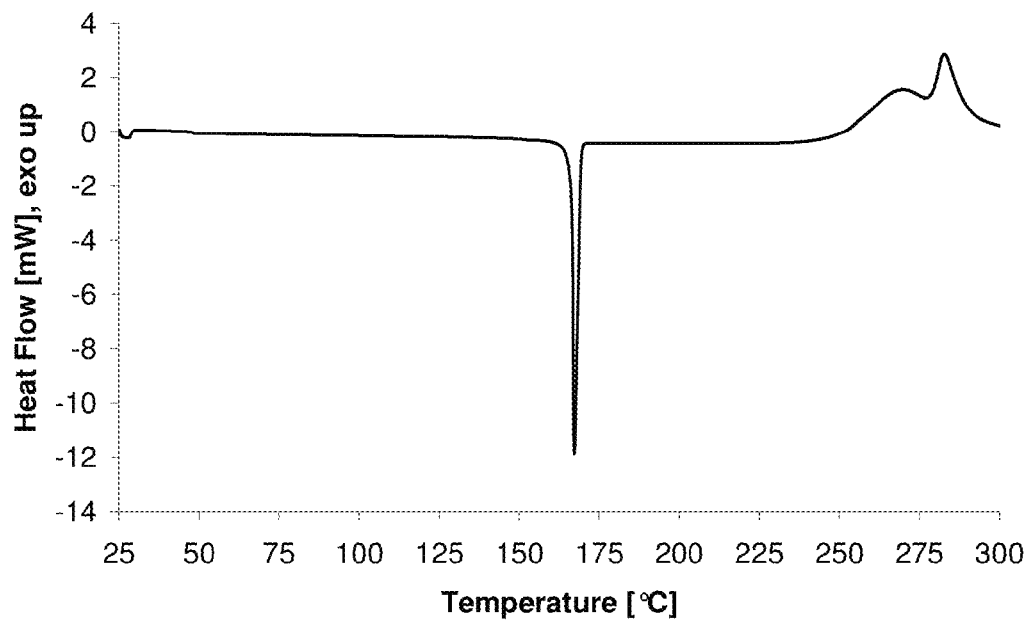
FIG. 24: DSC scan of Form B1
Figure 25:
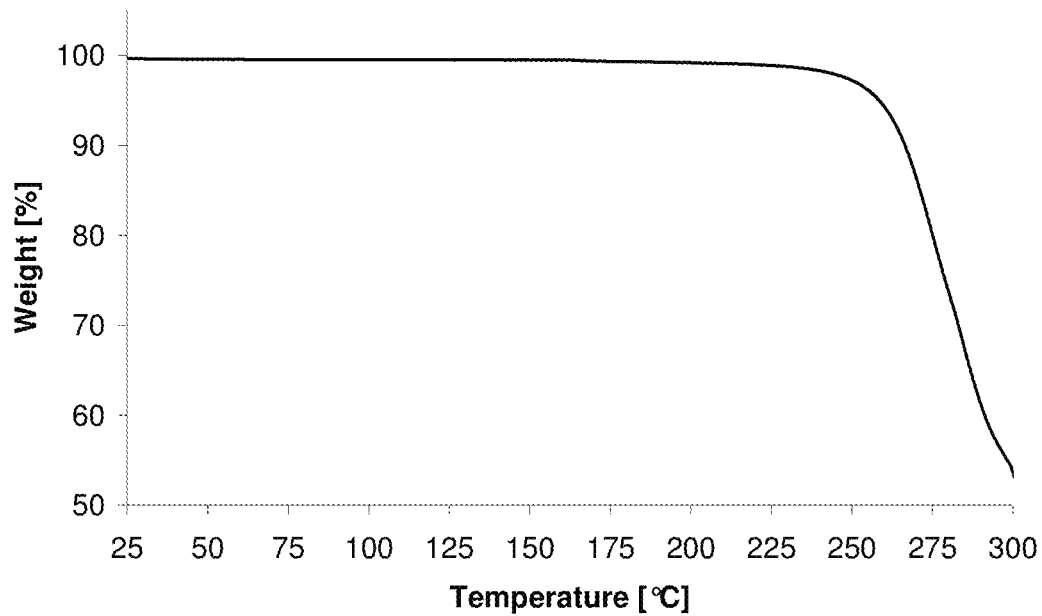
FIG. 25: TGA scan of Form B1

It could be shown that Form B1 is a crystalline anhydrous form, which is further characterised by the following physical properties:

Thermal behaviour of Form B1 shows a melting peak at approx. 165° C., with very small weight loss up to this temperature only. DSC and TGA profiles are displayed in FIGS. 24 and 25, respectively. DSC scan of Form B1 was acquired on a Mettler-Toledo DSC 821 with a heating rate of 5 K/min, using nitrogen purge gas at 50 mL/min. TGA scan of Form B1 was acquired on a Mettler-Toledo TGA 851 with a heating rate of 5 K/min, using nitrogen purge gas at 50 mL/min.

Figure 26:
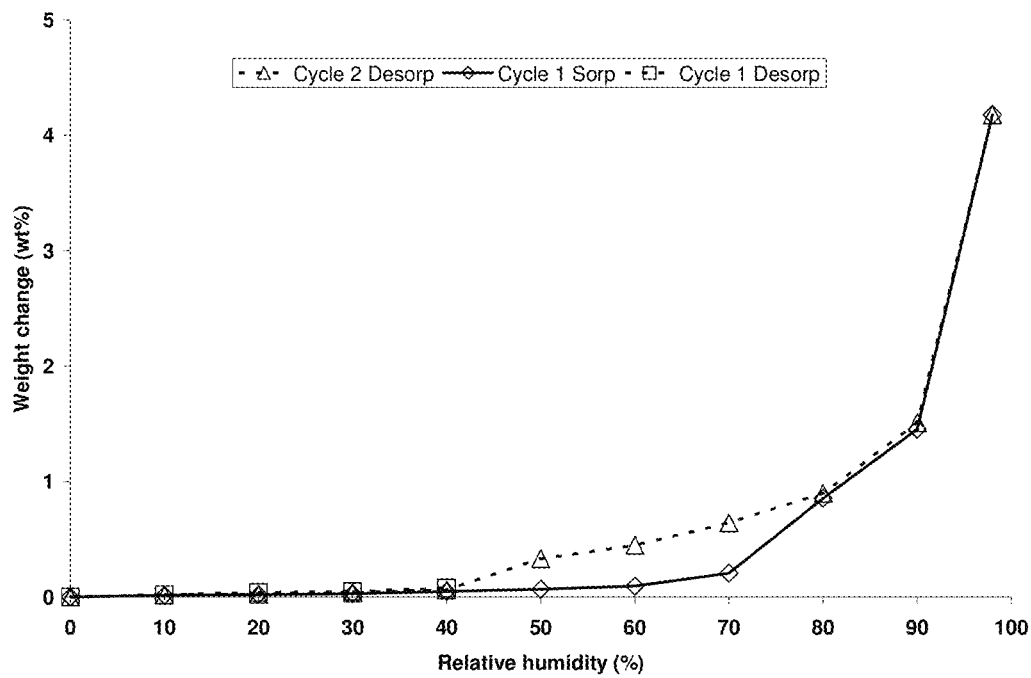
FIG. 26: Water Vapour Sorption Isotherm (25° C.) of Form B1

Water Vapour Sorption behaviour shows small water uptake levels<1 wt % in the relative humidity (RH) range 0-80% RH, and slightly enhanced water uptake at elevated RH. Form A1 can be classified as slightly hygroscopic acc. to Ph. Eur. criteria. Water Vapor Sorption isotherm (25° C.) of Form B1 is displayed in FIG. 26. Water Vapour Sorption isotherm was acquired on a DVS-1 System from SMS.

From solvent-mediated competitive slurry conversion experiments with binary phase mixtures of forms B1 and B2 in different solvents at ambient and at 50° C., Form B1 is clearly shown to result as solid-state residue at the expense of Form B2, thus confirming Form B1 as thermodynamically more stable free base form (see Example 6).

Solubility in USP phosphate buffer (pH 7.4) at 37° C. was determined to be approx. 50 μg/mL (see Example 7).

Overall, Form B1 reveals very good solid-state properties (good crystallinity, slightly hygroscopic only, sufficient thermal stability), which are favourable properties for solid dosage formulations.

Moreover, Form B1 can be considered as thermodynamically stable crystalline form of the free base.

4.2 Processes for the Preparation of B1

4.2.1 Method 1

Approx. 260 g of Compound C hydrochloride salt were dispersed in 6.5 L Water at RT, and stirred for 5 minutes. After addition of approx. 598 mL aqueous NaOH solution (1 N), a thick suspension is formed. The suspension is further agitated for approx. 10 minutes, before approx. 2.6 L Ethylacetate are added. The dispersion is further agitated for 20 minutes at RT, and is then filtrated and washed twice with approx. 260 mL water. The resulting filter residue is then dried under vacuum at 40° C. overnight.

4.2.2 Method 2

Approx. 20 mg of Compound C form B1 were dispersed in 1 mL 2-Propanol at RT. The dispersion was heated to 60° C., resulting in a clear solution, which was further filtrated over a 0.2 μm syringe filter. The clear warm solution was then cooled down to 4° C. at 0.1° C./min, resulting in a dispersion with crystals. Crystals were separated by filtration from the mother liquor, and left open at ambient conditions to evaporate residual solvents.

4.2.3 Method 3

Approx. 20 mg of Compound C form B1 were dispersed in 1 mL n-Butanol at RT. The dispersion was heated to 60° C., resulting in a clear solution, which was further filtrated over a 0.2 µm syringe filter. The clear warm solution was then cooled down to 4° C. at 0.1° C./min, resulting in a dispersion with crystals. Crystals were separated by filtration from the mother liquor, and left open at ambient conditions to evaporate residual solvents.

4.2.4 Method 4

Approx. 20 mg of Compound C form B1 were dispersed in 2 mL Methylethylketone at RT. The dispersion was heated to 60° C., resulting in a clear solution, which was further filtrated over a 0.2 µm syringe filter. The clear warm solution was then cooled down to 4° C. at 0.1° C./min, resulting in a dispersion with crystals. Crystals were separated by filtration from the mother liquor, and left open at ambient conditions to evaporate residual solvents.

5. Free Base Form B2

5.1 Characterization of Form 82

5.1.1 X-ray powder diffractometry

Figure 27:
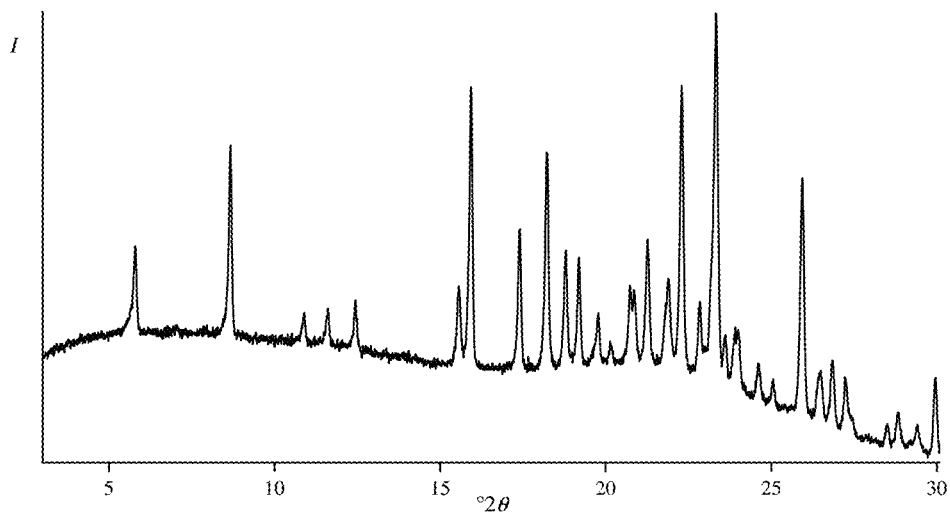
FIG. 27: Powder X-ray diffractogram of Form B2

A Powder X-Ray Diffraction pattern of Form B2 has been obtained by standard techniques at 301 K as described in the European Pharmacopeia 6$^{th}$ Edition chapter 2.9.33, which is shown in FIG. 27.

A list of characteristic X-ray peaks derived from this pattern is provided in Table XVII:

| No. | °2θ (Cu-Kα$_1$ radiation) ± 0.2° |
|---|---|
| 1 | 5.8 |
| 2 | 8.7 |
| 3 | 10.9 |
| 4 | 11.6 |
| 5 | 15.6 |
| 6 | 15.9 |
| 7 | 17.4 |
| 8 | 18.2 |
| 9 | 18.8 |
| 10 | 19.2 |
| 11 | 19.8 |
| 12 | 20.2 |
| 13 | 20.7 |
| 14 | 21.3 |
| 15 | 22.3 |
| 16 | 22.9 |
| 17 | 23.3 |
| 18 | 23.6 |
| 19 | 24.6 |
| 20 | 25.0 |
| 21 | 26.0 |
| 22 | 30.0 |

The most significant X-ray peaks from Table XVII are listed in Table XVIII:

| No. | °2θ (Cu-Kα$_1$ radiation) ± 0.2° |
|---|---|
| 1 | 8.7 |
| 2 | 15.9 |
| 3 | 17.4 |
| 4 | 18.2 |
| 5 | 18.8 |
| 6 | 19.2 |
| 7 | 21.3 |
| 8 | 22.3 |
| 9 | 23.3 |
| 10 | 26.0 |

Therefore, in a preferred aspect the present invention relates to crystalline form B2 having characteristic peaks at the 2θ angles provided in Table XVII.

In a more preferred aspect the invention relates to form B2 having characteristic peaks at the 2θ angles provided in Table XVIII.

Figure 28:
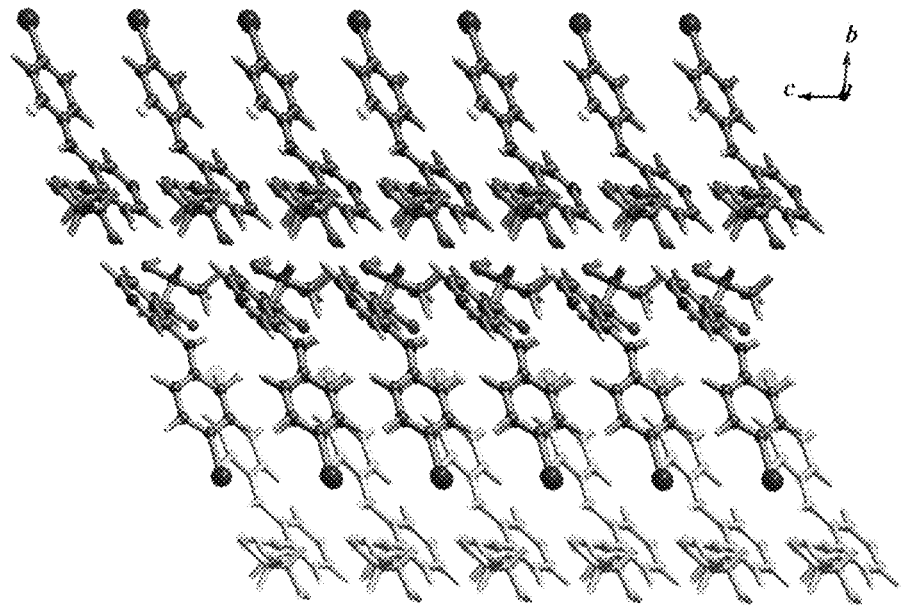
FIG. 28: Crystal structure of Form A2 (calculated from Powder data)

X-Ray Structural data were calculated from powder X-Ray data of Form B2 as shown in FIG. 28.

Form B2 crystallises in the chiral triclinic space group P1 with the lattice parameters a=11.7±0.1 Å, b=15.7±0.1 Å, c=4.8±0.1 Å, α=92.2±0.5°, β=101.3±0.5°, γ=102.9±0.5° at 301 K. From the crystal structure it is obvious that Form B2 represents an anhydrous form.

In a specific aspect, the invention relates to a crystalline form of the free base of Compound C characterized by these crystallographic parameters.

5.1.2 Vibrational Spectroscopy

Form B2 can be further characterized by infrared and Raman-spectroscopy. FT-Raman and FT-IR spectra have been obtained by standard techniques as described in the European Pharmacopeia 6$^{th}$ Edition chapter 2.02.24 and 2.02.48. For measurement of the FT-IR and FT-Raman-spectra a Bruker Vector 22 and a Bruker RFS 100 spectrometer have been used. FT-IR spectra have been base-line corrected using Bruker OPUS software. FT-Raman spectra have been vector normalized using the same software.

Figure 29:
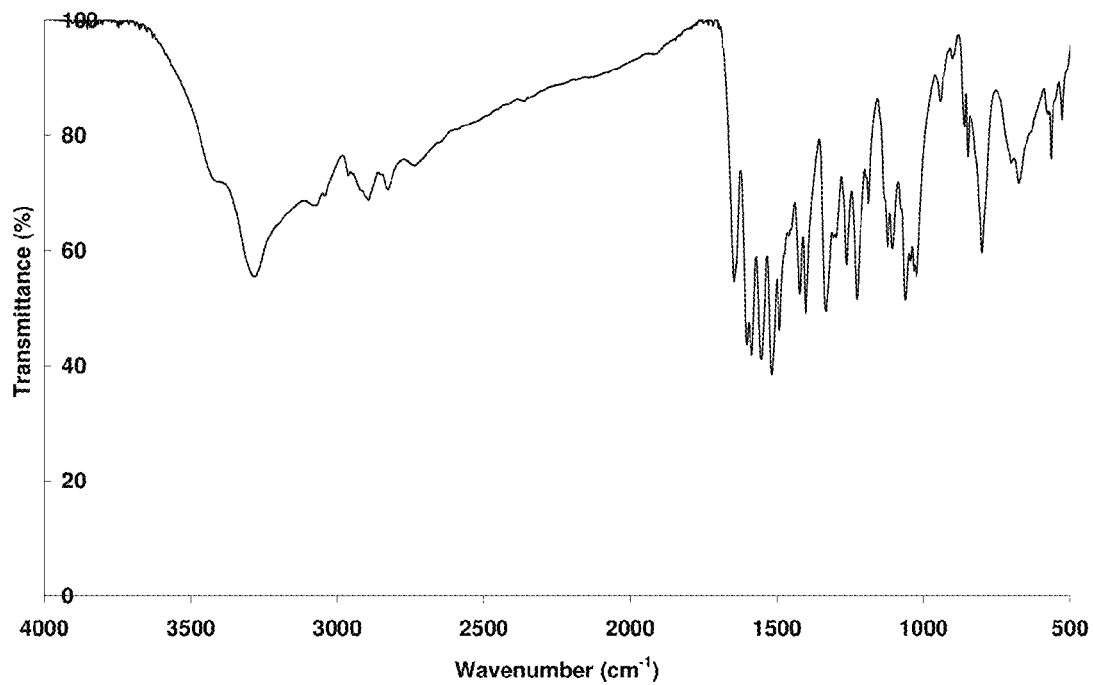
FIG. 29: FTIR spectrum of Form B2

An FT-IR spectrum has been obtained using a KBr pellet as sample preparation technique. The FT-IR spectrum is shown in FIG. 29 from which band positions are given below.

Form B2 IR band positions (±2 cm$^{-1}$, relative intensity*)
3287 cm$^{-1}$ (m), 2893 cm$^{-1}$ (w), 1646 cm$^{-1}$ (m), 1603 cm$^{-1}$ (s), 1586 cm$^{-1}$ (s), 1554 cm$^{-1}$ (s), 1518 cm$^{-1}$ (s), 1422 cm$^{-1}$ (m), 1401 cm$^{-1}$ (m), 1333 cm$^{-1}$ (s), 1227 cm$^{-1}$ (m), 1106 cm$^{-1}$ (m), 1062 cm$^{-1}$ (m), 1023 cm$^{-1}$ (m)

*"s"=strong (transmittance<50%), "m"=medium (50%<transmittance≤70%), "w"=weak (transmittance>70%)

Figure 30:
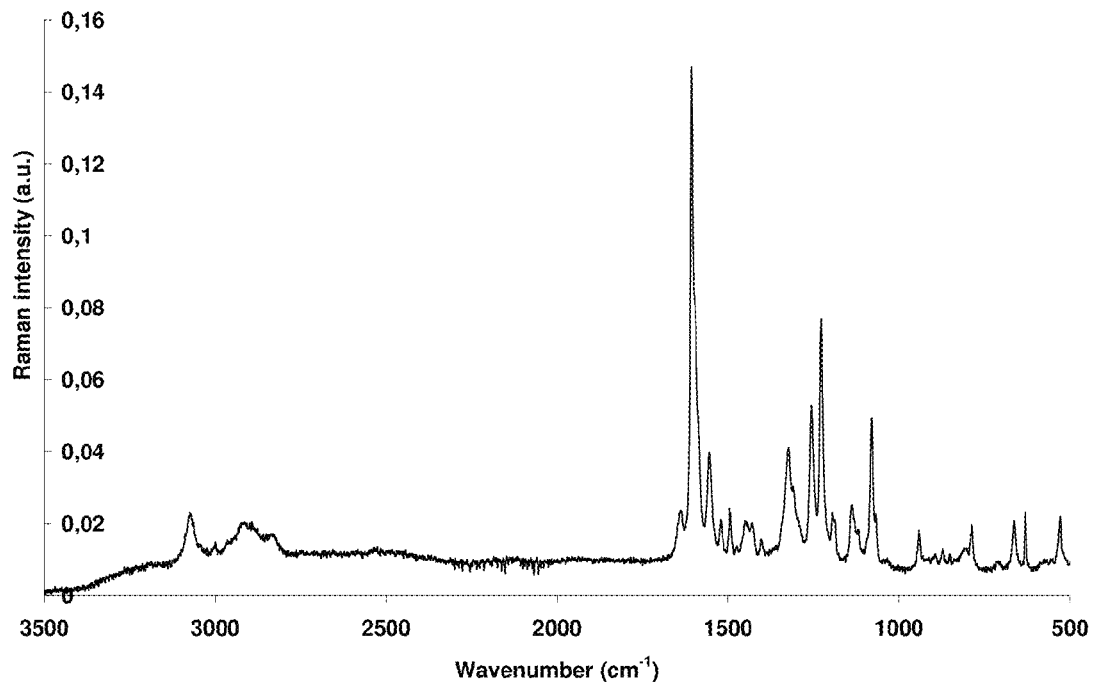
FIG. 30: FT Raman spectrum of Form B2

An FT-Raman spectrum is shown in FIG. 30 from which band positions were derived as given below.

Form B2 Raman band positions (±2 cm$^{-1}$, relative intensity*):
3074 cm$^{-1}$ (w), 2915 cm$^{-1}$ (w), 1607 cm$^{-1}$ (s), 1555 cm$^{-1}$ (m), 1322 cm$^{-1}$ (m), 1255 cm$^{-1}$ (m), 1228 cm$^{-1}$ (m), 1137 cm$^{-1}$ (m), 1079 cm$^{-1}$ (m), 941 cm$^{-1}$ (w), 787 cm$^{-1}$ (w), 630 cm$^{-1}$ (w), 527 cm$^{-1}$ (w)

*"s"=strong (relative Raman intensity≥0.1), "m"=medium (0.1>relative Raman intensity≥0.02), "w"=weak (relative Raman intensity<0.02)

5.1.3 Other Analytical Methods

It could be shown that Form B2 is a crystalline anhydrous form, which is further characterised by the following physical properties:

Thermal behaviour of Form B2 can be differentiated in two different morphological types, i.e. depending on particle properties of respective form B2 samples:
a) Morphological Type 1 shows a melting peak at approximately 145° C., overlapped by immediate re-crystallisation at approx. 155° C., and subsequent melting of the recrystallised phase B1 at approx. 165° C. Only small weight loss is observed up to the melting temperature of the original phase.
b) Morphological Type 2 shows an exothermic phase transition to form B1 at approx. 137° C., and subsequent melting of the formed phase at approx. 166° C. Only small weight loss is observed up to the phase transition temperature.

Figure 31:
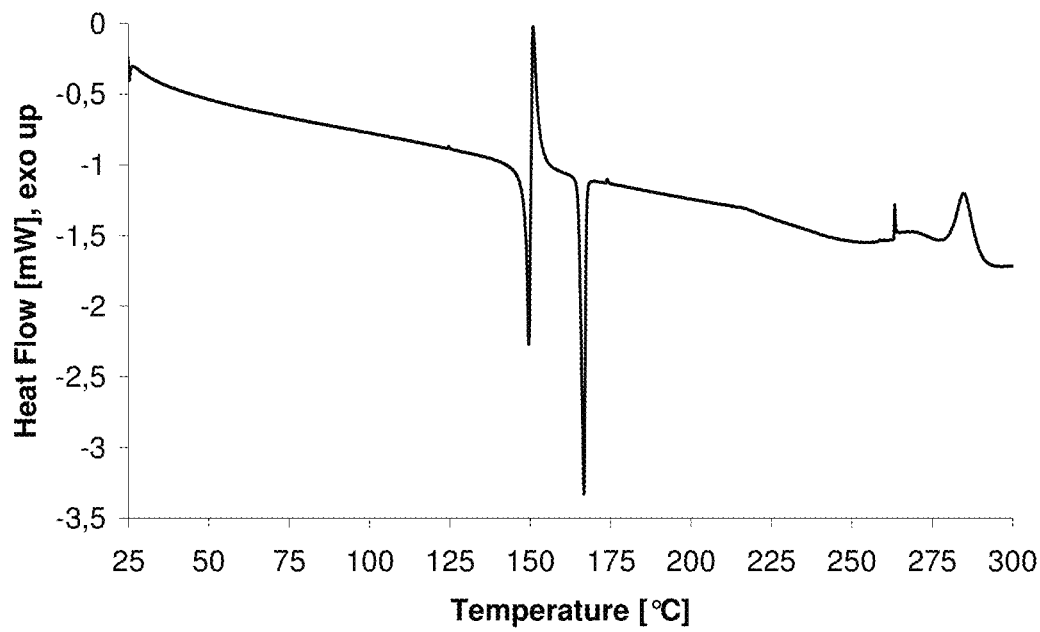
FIG. 31: DSC scan of Form B2 (Morphological Type 1)
Figure 32:
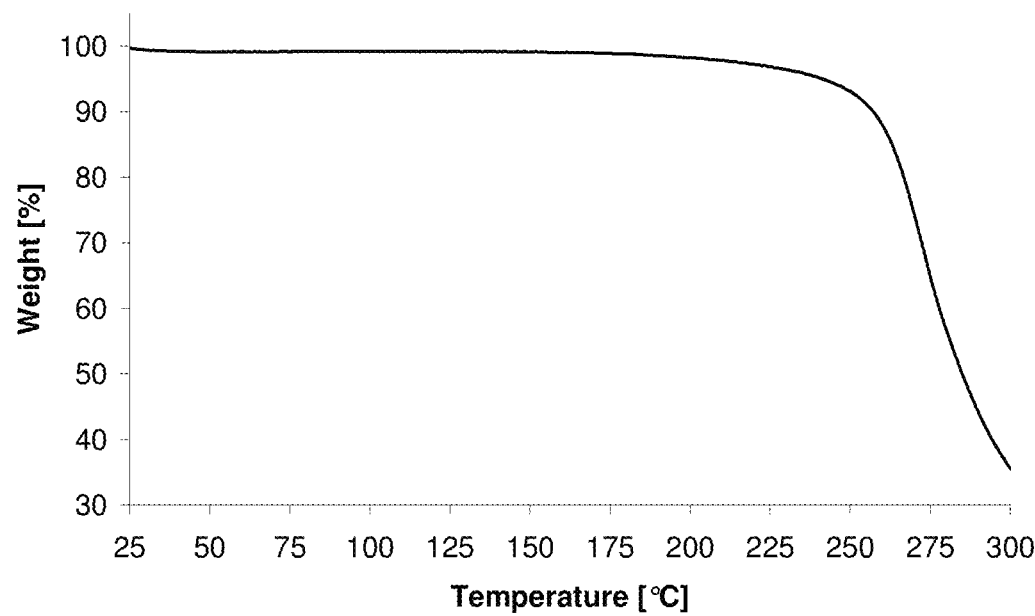
FIG. 32: TGA scan of Form B2 (Morphological Type 1)
Figure 33:
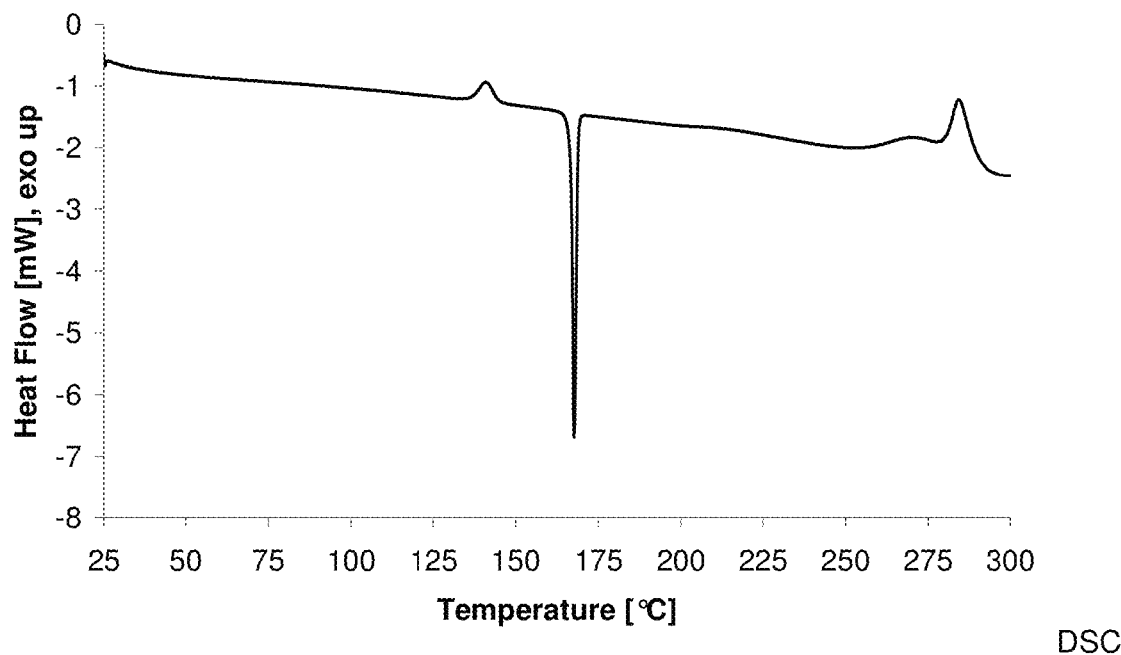
FIG. 33: DSC scan of Form B2 (Morphological Type 2)
Figure 34:
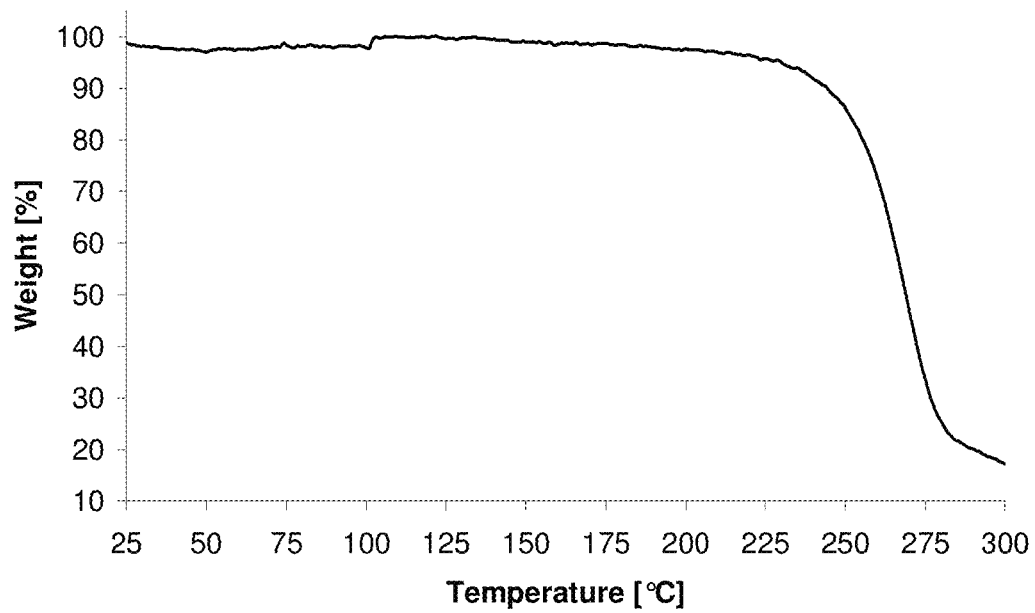
FIG. 34: TGA scan of Form B2 (Morphological Type 2)

DSC scans of Form B2 Type 1, as shown in FIGS. 31 and 33, were acquired on a Mettler-Toledo DSC 821 with a heating rate of 5 K/min, using nitrogen purge gas at 50 mL/min. TGA scans of Form B2 Type 2, as shown in FIGS. 32 and 34, were acquired on a Mettler-Toledo TGA 851 with a heating rate of 5 K/min, using nitrogen purge gas at 50 mL/min.

Figure 35:
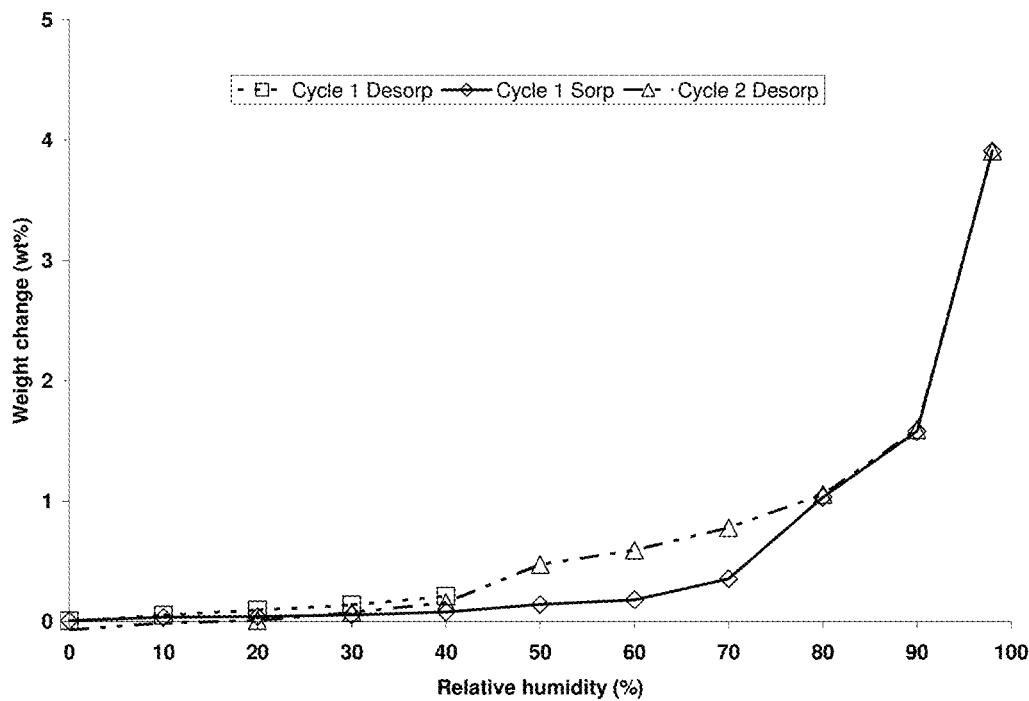
FIG. 35: Water Vapour Sorption Isotherm (25° C.) of Form B2

Water Vapour Sorption behaviour shows small water uptake levels ~1 wt % in the relative humidity (RH)

range 0-80% RH, and slightly enhanced water uptake at elevated RH (FIG. 35). Form B2 can be classified as slightly hygroscopic acc. to Ph. Eur. criteria. Water Vapor Sorption isotherm (25° C.) of Form B2 is displayed below. Water Vapour Sorption isotherm was acquired on a DVS-1 System from SMS.

Solubility in USP phosphate buffer (pH 7.4) at 37° C. was determined to be approx. 70 µg/mL (see Example 7).

Overall, Form B2 reveals good solid-state properties (crystallinity, slightly hygroscopic, sufficient thermal stability), which are favourable properties for solid dosage formulations.

5.2 Processes for the Preparation of 82

5.2.1 Method 1

Approximately 10 mg of Compound C (free base) crystalline form B1 were dissolved in approx. 1 mL of a binary mixture of Toluene:Methanol (1:1, v:v) at 50° C. Solutions were filtered through 0.2 µm syringe filters into 4 mL glass vials, and left open at 50° C. until full evaporation of the solvent mixture was completed. The resulting crystals were gently dispersed into a powder using a spatula.

5.2.2 Method 2

Approximately 10 mg of Compound C (free base) crystalline form B1 were dissolved in approx. 1 mL of a binary mixture of Toluene:Ethanol (1:1, v:v) at 50° C. Solutions were filtered through 0.2 µm syringe filters into 4 mL glass vials, and left open at 50° C. until full evaporation of the solvent mixture was completed. The resulting crystals were gently dispersed into a powder using a spatula.

5.2.3 Method 3

Approximately 10 mg of Compound C (free base) crystalline form B1 were dissolved in approx. 2.5 mL of a binary mixture of Toluene:Acetone (1:1, v:v) at 50° C. Solutions were filtered through 0.2 µm syringe filters into 4 mL glass vials, and left open at 50° C. until full evaporation of the solvent mixture was completed. The resulting crystals were gently dispersed into a powder using a spatula.

5.2.4 Method 4

Approximately 10 mg of Compound C (free base) crystalline form B1 were dissolved in approx. 4 mL of a binary mixture of Toluene:Methylethylketone (1:1, v:v) at 50° C. Solutions were filtered through 0.2 µm syringe filters into 4 mL glass vials, and left open at 50° C. until full evaporation of the solvent mixture was completed. The resulting crystals were gently dispersed into a powder using a spatula.

5.2.5 Method 5

Approximately 10 mg of Compound C (free base) crystalline form B1 were dissolved in approx. 8.5 mL of a binary mixture of Toluene:Ethylacetate (1:1, v:v) at 50° C. Solutions were filtered through 0.2 µm syringe filters into 4 mL glass vials, and left open at 50° C. until full evaporation of the solvent mixture was completed. The resulting crystals were gently dispersed into a powder using a spatula.

5.2.6 Method 6

Approximately 10 mg of Compound C (free base) crystalline form B1 were dissolved in approx. 10.5 mL of a binary mixture of Toluene:Chloroforme (1:1, v:v) at 50° C. Solutions were filtered through 0.2 µm syringe filters into 4 mL glass vials, and left open at 50° C. until full evaporation of the solvent mixture was completed. The resulting crystals were gently dispersed into a powder using a spatula.

5.2.7 Method 7

Approximately 10 mg of Compound C (free base) crystalline form B1 were dissolved in approx. 2.5 mL of a binary mixture of Toluene:Dioxane (1:1, v:v) at 50° C. Solutions were filtered through 0.2 µm syringe filters into 4 mL glass vials, and left open at 50° C. until full evaporation of the solvent mixture was completed. The resulting crystals were gently dispersed into a powder using a spatula.

5.2.8 Method 8

Approximately 10 mg of Compound C (free base) crystalline form B1 were dissolved in approx. 4 mL of Toluene at ambient conditions (approx. 23° C.). Solutions were filtered through 0.2 µm syringe filters into 4 mL glass vials, and left open at ambient conditions until full evaporation of the solvent was completed. The resulting crystals were gently dispersed into a powder using a spatula.

6. Solvent-Mediated Competitive Slurry Conversion Experiments with Binary Phase Mixtures of Forms B1+B2

Approximately 10 mg of Compound C (free base) crystalline form B1 and approx. 5 mg of Compound C (free base) crystalline form B2 were dispersed in 200-1000 µL solvent in 4-mL glass vials. A PTFE-coated magnetic stirring bar was inserted into the dispersions, and the vials were tightly closed with a screw cap containing a septum. Dispersions were agitated for 5 days on a magnetic stirrer at ambient conditions (~23° C.) and 50° C., respectively. Dispersions were then vacuum-filtrated over a Whatman paper filter, and collected filter residues were analysed by X-Ray-Diffraction for identity with the initially used materials.

Results from competitive slurry conversion experiments are summarised below.

| Binary mixture B1:B2 (approx. 2:1, wt/wt) slurried 5 days in | RT | 50° C. |
| --- | --- | --- |
| Water | B1 | B1 |
| 2-Propanol | B1 | B1 |
| Ethanol | B1 | B1 |
| THF | B1 | B1 |
| Acetone | B1 | B1 |
| Acetonitrile | B1 | B1 |
| Ethlyacetate | B1 | B1 |
| MTBE | B1 | B1 |
| Chloroforme | B1 | B1 |
| n-Hexane | B1 | B1 |

It can clearly be seen that form B1 results as solid-state residue from all competitive slurry conversion experiments starting from mixtures with B2, clearly revealing form B1 as more stable form between RT and 50° C.

7. Determination of Thermodynamic Solubility of Forms B1 and B2 in Water

Approximately 17 mg of Compound C (free base) crystalline form B1 were dispersed in 2 mL USP Phosphate Buffer (pH 7.4) in Whatman Uniprep Syringless Filter vials in duplicate preparations.

Approximately 17 mg of Compound C (free base) crystalline form B2 were dispersed in 2 mL USP Phosphate Buffer (pH 7.4) in Whatman Uniprep Syringless Filter vials in duplicate preparations.

All dispersions were agitated at 37° C. for 24 hours. Dispersions were then filtered via the internal filter of the Uniprep vials, and clear filtrates were analysed by HPLC for dissolved quantities of Compound C.

Solid state residues were analysed by X-Ray-Diffraction for identity with the initially used materials.

Results from solubility determinations are summarised below.

| Investigated Form | Solubility (µg/mL) | Solid-state residue |
| --- | --- | --- |
| Free Base Form B1 | #1: 49 | #1 + #2: |
|  | #2: 56 | Free Base Form B1 |
| Free Base Form B2 | #1: 71 | #1 + #2: |
|  | #2: 67 | Free Base Form B1 |

Although both preparations of form B2 undergo phase conversion to form B1 upon longterm slurrying in PBS buffer, it can clearly be seen that form B2 exhibits an increased supersaturated solubility level compared to form B1.

8. Solvates of the Free Base of Compound C

In addition to Forms B1 and B2 described above a series of solvate forms of the free base of C were also identified, which were not further characterised in terms of physical properties.

8.1 Acetic Acid Solvate Form B-S1

Figure 36:
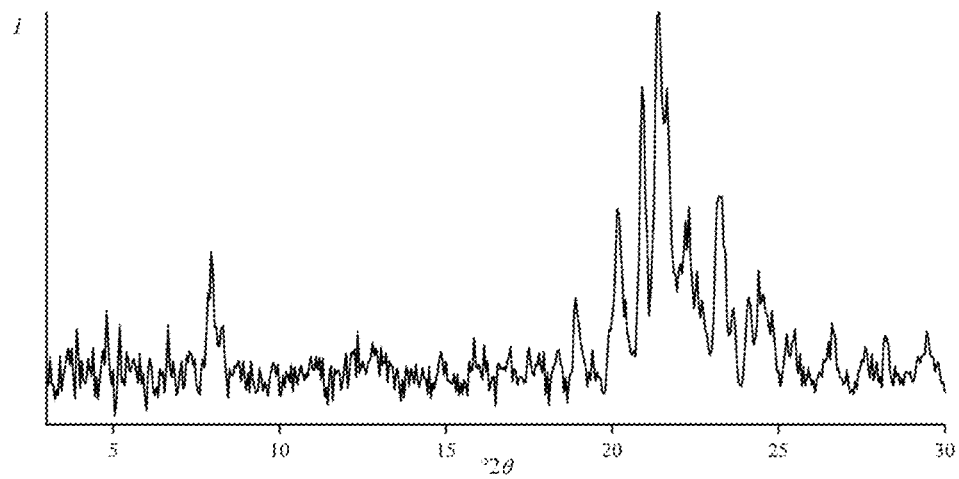
FIG. 36: Powder X-ray diffractogram of Form B-S1

From the powder X-ray diffractogram of Form B-S1 shown in FIG. 36 the following peaks were derived—Table XIX:

| No. | °2θ (Cu-Kα$_1$ radiation) ± 0.2° |
|---|---|
| 1 | 8.0 |
| 2 | 18.9 |
| 3 | 20.2 |
| 4 | 20.9 |
| 5 | 21.4 |
| 6 | 21.6 |
| 7 | 22.2 |
| 8 | 23.2 |
| 9 | 23.3 |
| 10 | 23.7 |
| 11 | 24.1 |
| 12 | 24.4 |
| 13 | 24.6 |
| 14 | 24.8 |
| 15 | 25.4 |
| 16 | 26.5 |
| 17 | 26.6 |

8.2 Dioxane Solvate Form B-S2

Figure 37:
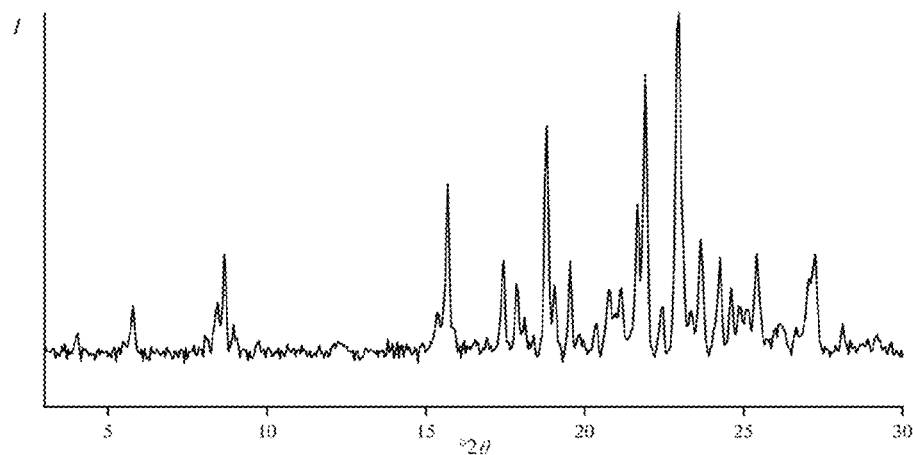
FIG. 37: Powder X-ray diffractogram of Form B-S2
Figure 38:
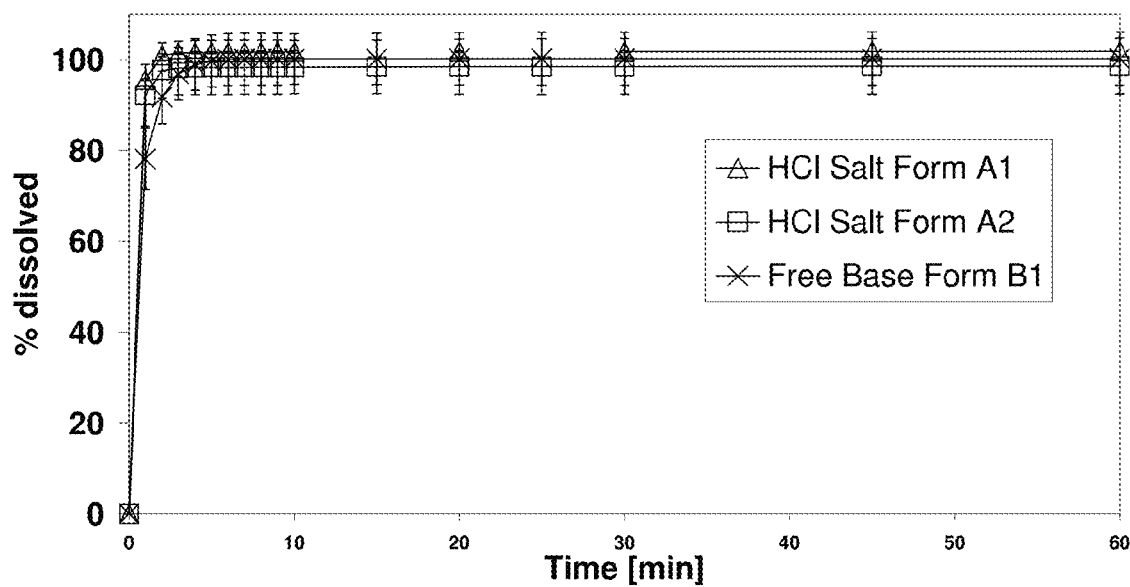
FIG. 38: Dissolution of Compound C solid state forms at pH 1.2
Figure 39:
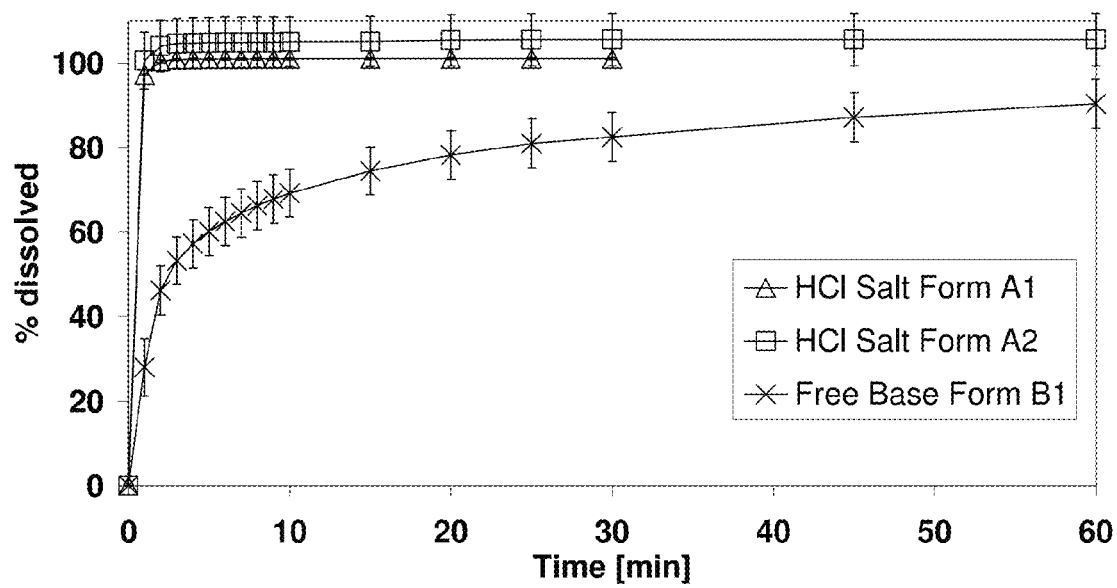
FIG. 39: Dissolution of Compound C solid state forms at pH 3.0
Figure 40:
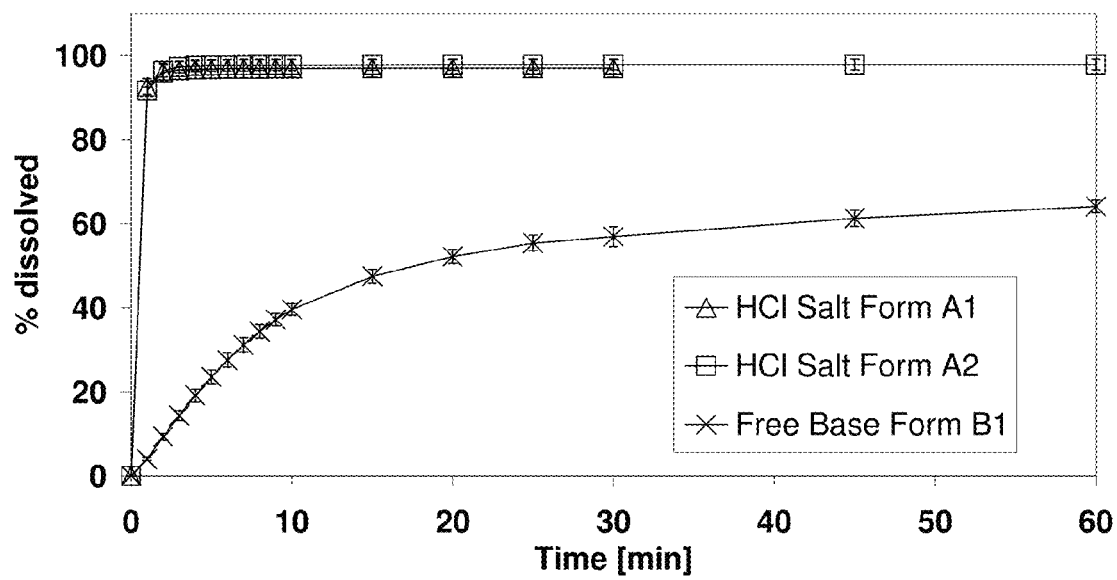
FIG. 40: Dissolution of Compound C solid state forms at pH 5.0
Figure 41:
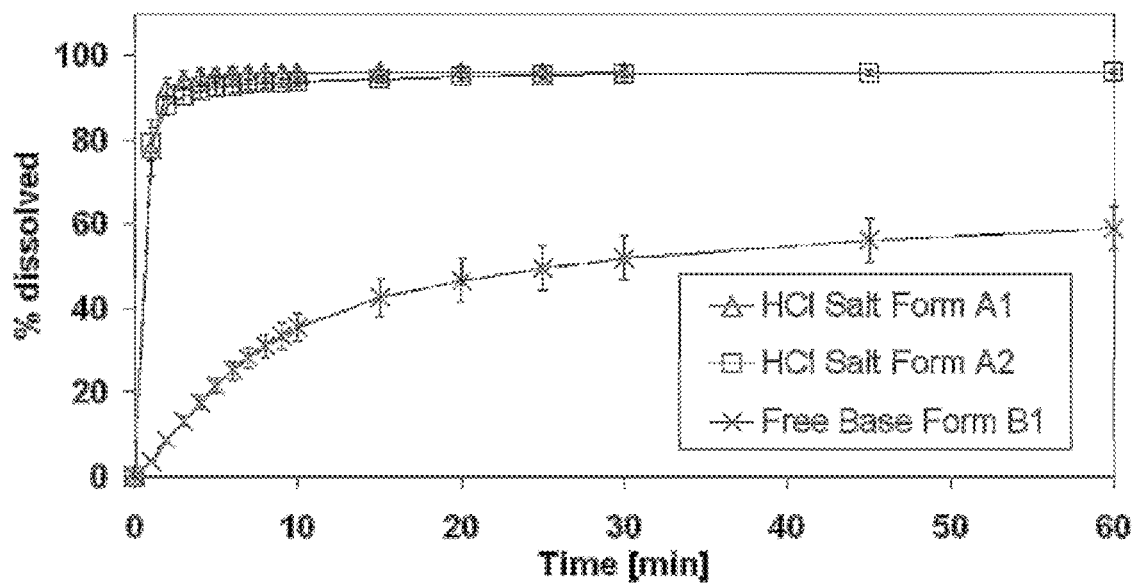
FIG. 41: Dissolution of Compound C solid state forms at pH 6.8

From the powder X-ray diffractogram of Form B-S2 shown in FIG. 37 the following peaks were derived—Table XX:

| No. | °2θ (Cu-Kα$_1$ radiation) ± 0.2° |
|---|---|
| 1 | 4.0 |
| 2 | 5.8 |
| 3 | 8.7 |
| 4 | 15.4 |
| 5 | 15.7 |
| 6 | 17.4 |
| 7 | 17.9 |
| 8 | 18.8 |
| 9 | 19.0 |
| 10 | 19.6 |
| 11 | 20.8 |
| 12 | 21.2 |
| 13 | 21.7 |
| 14 | 21.9 |
| 15 | 22.4 |
| 16 | 23.0 |
| 17 | 23.7 |
| 18 | 24.2 |
| 19 | 25.4 |
| 20 | 27.1 |
| 21 | 27.3 |

9. Solubility Determinations of HCl Salt Forms Vs. Free Base

Approximately 10 mg of Compound C hydrochloride salt form A1 were dispersed in 2 mL DI water in Whatman Uniprep Syringless Filter vials. Approximately 10 mg of Compound C hydrochloride salt form A2 were dispersed in 2 mL DI water in Whatman Uniprep Syringless Filter vials. Approximately 10 mg of Compound C free base form were dispersed in 2 mL DI water in Whatman Uniprep Syringless Filter vials.

All dispersions were agitated at 37° C. for 24 hours. Dispersions were then filtered via the internal filter of the Uniprep vials, and clear filtrates were analysed by HPLC for dissolved quantities of Compound C.

Solid state residues were analysed by X-Ray-Diffraction for identity with the initially used materials.

Results from solubility determinations are summarized below.

| Compound | Solubility (mg/mL) | | Solid-state Residue |
|---|---|---|---|
| HCl salt Form A1 | 2.8 | (Water) | Free base Form B1 |
|  | 43.6 | (0.1 N HCl) | HCl salt Form A1 |
| HCl salt Form A2 | 2.5 | (Water) | Free base Form B1 |
|  | >20 | (0.1 N HCl) | No residue obtained |
| Free Base Form B1 | <0.1 | (Water) | Free base Form B1 |
|  | 17.5 | (0.1 N HCl) | HCl salt Form A1 |

Both hydrochloride salt forms exhibit significantly higher solubility levels in 0.1. N HCl and DI Water compared to free base.

10. Dissolution Studies of HCl Salt Forms Vs. Free Base

Approximately 10 mg of Forms A1, A2 or B1, respectively, were accurately weighed and blended with 2 g glass beads in a Vortex mixer. The blends were then placed into a powder cell of a Flow-Through-Cell system. Dissolution studies were performed at 37° C. over 30-60 minutes at a constant flow rate of 16 mL/min. Fractions of dissolution medium after passing the Flow-Through-Cell were collected in 1 minute intervals in the first 10 minutes, in 5 minute intervals from 10-30 minutes, and in 15 minute intervals from 30-60 minutes. Dissolved levels of API in each fraction were analysed by HPLC. In dissolution experiments with HCl salt forms at pH 5.0 and pH 6.8, free base fractions which precipitated over time from the initially clear solutions in the collected dissolution fractions were re-dissolved by addition of sulphuric acid prior to HPLC analysis. All experiments were performed as triplicate preparations, with results reported as mean values from triplicates, and error bars as single standard deviations from the triplicates.

Results from API Dissolution studies are displayed in FIGS. 38, 39, 40 and 41.

pH 1.2:

The following % dissolved levels are obtained after 30 minutes:

HCl Salt Form A1: 100%
HCl Salt Form A2: 99%
Free base Form B1: 100% pH 3.0:

The following % dissolved levels are obtained after 30 minutes:

HCl Salt Form A1: 100%
HCl Salt Form A2: 100%
Free base Form B1: 83% pH 5.0:

The following % dissolved levels are obtained after 30 minutes:

HCl Salt Form A1: 97%
HCl Salt Form A2: 98%
Free base Form B1: 57% pH 6.8:

The following % dissolved levels are obtained after 30 minutes:

HCl Salt Form A1: 96%
HCl Salt Form A2: 96%
Free base Form B1: 52%

All solid state forms of Compound C, including any salts and solvates, and all manufacturing methods described herein are also comprised by, and object of, the present invention.

The invention claimed is:

1. A solid state form of N—((S)-2,3-Dihydroxy-propyl)-3-(2-fluoro-4-iodo-phenylamino)-isonicotinamide or its pharmaceutically acceptable salts, in which the solid state form or its pharmaceutically acceptable salt is a crystalline form.

2. The solid state form according to claim 1, in which the pharmaceutically acceptable salt is the mono hydrochloride.

3. The solid state form according to claim 1, which is the free base of N—((S)-2,3-Dihydroxy-propyl)-3-(2-fluoro-4-iodo-phenylamino)-isonicotinamide.

4. A solid state form A1 according to claim 2, having characteristic Cu—K$\alpha_1$ X-ray peaks at 2θ angles corresponding to 5.5±0.2, 16.8±0.2, 18.5±0.2, 19.1±0.2, 22.6±0.2, 23.0±0.2, 24.9±0.2, 25.2±0.2, 28.4±0.2, 29.2±0.2 degrees.

5. A solid state form A1 according to claim 2, having characteristic Cu—K$\alpha_1$ X-ray peaks at 2θ angles corresponding to one or more of the following lists of peaks:
   a) 5.5±0.2, 16.8±0.2, 19.5±0.2, 23.0±0.2 degrees;
   b) 5.5±0.2, 18.5±0.2, 19.1±0.2, 28.4±0.2, 29.6±0.2 degrees;
   c) 15.9±0.2, 19.1±0.2, 24.9±0.2 degrees.

6. A solid state form A1 according to claim 2, having the space group P2$_1$ with the lattice parameters a=9.6±0.1 Å, b=11.2±0.1 Å, c=16.6±0.1 Å, and β=104.4±0.5° (α=γ=90°) when measured at 301 K.

7. A solid state form A2 according to claim 2, having characteristic Cu—K$\alpha_1$ X-ray peaks at 2θ angles corresponding to 5.4±0.2, 9.6±0.2, 18.4±0.2, 18.6±0.2, 20.9±0.2, 21.6±0.2, 23.9±0.2, 24.4±0.2, 25.0±0.2, 26.0±0.2 degrees.

8. A solid state form A2 according to claim 2, having characteristic Cu—K$\alpha_1$ X-ray peaks at 2θ angles corresponding to one or more of the following lists of peaks:
   a) 18.4±0.2, 18.6±0.2, 19.2±0.2, 20.2±0.2, 21.6±0.2 degrees;
   b) 9.6±0.2, 11.3±0.2, 17.8±0.2, 23.9±0.2, 25.0±0.2 degrees.

9. A solid state form A2 according to claim 2, having the space group P2$_1$2$_1$2 with the lattice parameters a=32.3±0.1 Å, b=11.2±0.1 Å, c=4.8±0.1 Å, with α=β=γ=90°, when measured at 301 K.

10. A solid state form B1 according to claim 3, having characteristic Cu—K$\alpha_1$ X-ray peaks at 2θ angles corresponding 7.0±0.2, 14.0±0.2, 18.3±0.2, 19.0±0.2, 20.6±0.2, 21.2±0.2, 24.2±0.2, 25.1±0.2, 25.4±0.2, 27.9±0.2 degrees.

11. A solid state form B1 according to claim 3, having the space group P2$_1$2$_1$2$_1$ with the lattice parameters a=20.8±0.1 Å, b=15.7±0.1 Å, c=5.0±0.1 Å (α=β=γ=90° when measured at 301 K.

12. A solid state form B2 according to claim 3, having characteristic Cu—K$\alpha_1$ X-ray peaks at 2θ angles corresponding 8.7±0.2, 15.9±0.2, 17.4±0.2, 18.2±0.2, 18.8±0.2, 19.2±0.2, 21.3±0.2, 22.3±0.2, 23.3±0.2, 26.0±0.2 degrees.

13. A solid state form B2 according to claim 3, having the space group P1 with the lattice parameters a=11.7±0.1 Å, b=15.7±0.1 Å, c=4.8±0.1 Å, α=92.2±0.5°, β=101.3±0.5°, γ=102.9±0.5° when measured at 301 K.

14. A solid state form according to claim 1, as medicament.

15. A solid state form according to claim 1, for use in the treatment of cancer.

16. A pharmaceutical composition comprising a solid state form according to claim 1, as active ingredient, together with at least one pharmaceutically acceptable carrier.

* * * * *